United States Patent [19]
Kirpotin et al.

[11] Patent Number: 5,411,730
[45] Date of Patent: May 2, 1995

[54] MAGNETIC MICROPARTICLES

[75] Inventors: Dmitri Kirpotin; Daniel C. F. Chan, both of Denver; Paul A. Bunn, Jr., Evergreen, all of Colo.

[73] Assignee: Research Corporation Technologies, Inc., Tucson, Ariz.

[21] Appl. No.: 94,790

[22] Filed: Jul. 20, 1993

[51] Int. Cl.$^6$ .................... A61B 5/055; A61K 31/715
[52] U.S. Cl. .................... 424/322; 428/403; 423/633; 423/634; 436/173; 436/806; 128/653.4; 514/6; 514/54; 514/59; 424/647
[58] Field of Search .................... 424/9; 428/403; 423/633, 634; 436/173, 806; 128/653.4, 654; 514/6, 54, 59

[56] References Cited

U.S. PATENT DOCUMENTS

| | | | |
|---|---|---|---|
| 4,101,435 | 7/1978 | Hasegawa | 252/62.53 |
| 4,106,488 | 8/1978 | Gordan | 128/1 R |
| 4,331,654 | 5/1982 | Morris | 424/38 |
| 4,452,773 | 6/1984 | Molday | 424/1.1 |
| 4,770,183 | 9/1988 | Groman | 128/654 |
| 4,827,945 | 5/1989 | Groman | 128/653 |
| 4,927,624 | 5/1990 | Bryant et al. | 424/9 |
| 4,951,675 | 8/1990 | Groman | 128/653.4 |
| 5,102,652 | 4/1992 | Groman et al. | 424/9 |
| 5,160,725 | 11/1992 | Pilgrimm | 424/9 |
| 5,160,726 | 11/1992 | Josephson et al. | 424/9 |
| 5,219,554 | 6/1993 | Groman et al. | 424/9 |
| 5,262,176 | 11/1993 | Palmacci et al. | 424/9 |
| 5,284,646 | 2/1994 | Menz et al. | 424/9 |

FOREIGN PATENT DOCUMENTS

| | | |
|---|---|---|
| 16184/92 | 3/1992 | Austria . |
| 0272091 | 6/1988 | European Pat. Off. . |
| WO04441-94A1 | 4/1991 | WIPO . |
| WO/9116080 | 10/1991 | WIPO . |

OTHER PUBLICATIONS

Chan, *Hyper. Oncol.* 1:367 (1992).
Kirpotin, et al. (1992), "In vitro Studies of Ferromagnetic Colloidal Particles in Radiofrequency Induced Hyperthermia," #3009, *Proceedings of the American Ass'n for Canc. Res.* 33:503.
Kirpotin, D. B. (1993), ASCO Abstract, "Colloidal Magnetic Iron Oxides with Improved Power Absorption Rates for Ferromagnetic Hyperthermia of Cancer".
De Cuyer et al. (1988) "Magnetoliposomes," *Eur. Biophys. J.* 15:311–319.
Chan, et al. (1993) "Synthesis and Evaluation of Colloidal Magnetic Iron Oxides for the Site-Specific Radio-frequency-Induced Hyperthermia of Cancer," *J. Magn. and Mag. Mat.* 122:374–378.
Pouliquen, et al. (1991) "Iron Oxide Nanoparticles for Use as an MRI Contrast Agent: Pharmacokinetics and Metabolism" *Mag. Res. Im.* 9:275–283.
Ferrucci, et al. (1991) "Iron Oxide-Enhanced MR Imaging of the Liver and Spleen: Review of the First 5 Years," pp. 943–995.

*Primary Examiner*—Gary E. Hollinden
*Attorney, Agent, or Firm*—Greenlee and Winner

[57] ABSTRACT

Superparamagnetic particles are provided for medical applications including hyperthermia techniques, localized heating and tissue-specific release of therapeutic agents, and magnetic resonance imaging contrast enhancement, comprising superparamagnetic iron oxide and a polymer such as dextran at a ratio of about 0.5 to 0.1 w/w of polymer to iron. The particles display at least one of the following magnetic properties: (a) specific power absorption rate greater than 300 w/g Fe; (b) initial magnetic susceptibility greater than 0.7 EMU/g Fe/Gauss; and (c) magnetic moment greater than $10^{-15}$ erg/Gauss.

13 Claims, 13 Drawing Sheets

MAGNETIC MICROPARTICLES

This intention was made with partial support of the U.S. National Institutes of Health grant No. 2531781. The U.S. government has certain right in this invention.

FIELD OF THE INVENTION

The invention is directed to magnetic particles prepared for medical applications including hyperthermia techniques, localized heating and tissue-specific release of therapeutic agents, and magnetic resonance imaging contrast enhancement.

BACKGROUND OF THE INVENTION

It has been recognized that when heat is applied to the areas of animal or human tissue containing malignant cells so as to increase the temperature of the area to 41°–45° C. a preferable decrease in the viability of malignant cells occurs. The decreased viability of the malignant cells results either in the cell death or cell sensitization to the effects of concomitant chemotherapy and/or radiation therapy and therefore is favorable for the tumor therapy. Such heat treatment of tissues is known as hyperthermia [1,2]. In the group of hyperthermia techniques called ferromagnetic hyperthermia, a particulate ferromagnetic material is confined within the treatment area and further exposed to the oscillating electromagnetic field. The confined ferromagnetic particles dissipate the energy of the field in the form of heat through various kinds of energy losses and therefore cause hyperthermia in the area of their confinement [3–16].

A variety of ferromagnetic microparticulate and colloidal materials have been reported for the use in ferromagnetic hyperthermia including: oxidized pentacarbonyl iron particles [3–5], iron powders [6,7], magnetite dispersions [8,9], ceramic-magnetic iron composites [10,11], alkali earth hexaferrites [12], dextran-ferrite [13,14], and oxidized dextran-magnetite compounds [15,16]. The magnetic properties of such particles have not been disclosed in terms of standard tests which would permit direct comparison of different preparations. The heating quality of the above materials are compared herein on the basis of available literature data or by our own measurements of the materials prepared according to the reported procedures. The heating quality of the ferromagnetics are expressed herein as their specific power absorption rate (SAR) defined as the amount of heat released by a unit weight of the material per unit time during exposure to an oscillating magnetic field of defined frequency and field strength. Physical considerations of the mechanisms involved in the dissipation of the electromagnetic field energy by these materials suggest that SAR is approximately proportional to the field frequency times field strength squared. Therefore for fair comparison we have normalized the heating rates to the frequency of 1 MHz and peak field strength of 100 Oersted.

The results of such comparison (Table 1) suggested that all previously disclosed materials require substantial tissue concentrations (more than 5–10 mg/gram of tissue) to provide effective heating. Materials based on precipitated iron oxides generally gave superior results compared with other types of ferromagnetics. Precipitated iron oxides are well-known in such applications as magnetic resonance imaging in diagnostic medicine [17,20,21], magnetic labeling and sorting of cells [18], and bone marrow purging for treatment of cancer patients [19]. These compounds were shown to produce little, if any, toxicity to animals and humans [20,21]. It has also been shown that dextran-coated iron oxide particles have excellent stability against aggregation and precipitation in physiological media [16,22,23]. A widely used procedure for precipitating iron oxide in the presence of dextran is described by Molday [23]. According to the Molday procedure, dextran (stabilizer) is first mixed with ferric and ferrous salts in aqueous solution; then the excess of aqueous ammonia (precipitant) is added to precipitate iron hydroxides, and the suspension is heat treated to convert hydroxides into magnetic iron oxide. Finally, the grossly aggregated fraction is separated by low speed centrifugation, and the remaining colloid is purified by dialysis and/or gel-filtration. As described below, magnetic particles prepared according to the present invention provide substantially increased tissue heating compared to previously disclosed particles. Therefore the particles of the present invention substantially reduce the amount of magnetic material required to achieve therapeutically useful heating.

The Molday procedure [23] includes:

1) combining of iron(II) and iron(III) chloride salts with the stabilizer (dextran) and precipitant (ammonia) in aqueous solution with agitation;

2) treatment of the reaction mixture at the temperature of 60°–65° C. for 15 min;

3) separation of larger aggregates by low-speed centrifugation; and 4) purification of magnetic particles by gel-filtration.

The heating properties of the resulting ferrocolloids are insufficient to make a qualitative improvement in the amount of ferrocolloid required for heating of a tumor in the radiofrequency electromagnetic (RF EM) fields of such frequency and amplitude that would not at the same time cause substantial background heating of the tissue itself. As explained in numerous publications [3–5, 11,12] such frequencies and amplitudes lie in the range of 0.05–1.2 MHz and 0–200 Oersted, respectively.

The use of magnetic microparticles has been heretofore hindered by the fact that injected particles are rapidly cleared from the bloodstream by reticuloendothelial (RES) cells, primarily in liver and spleen [27, 28, 29]. No successful method of overcoming this problem has been reported to date. The problem of RES-dependent blood clearance is also observed in site-specific drug delivery studies. It has been shown that large unicellular liposomes of 0.1–0.5 µm in size, enriched in sphingomyelin, phospholipids with high transition temperatures and exposed sugar moieties (e.g., phosphatidylinositol or sialogangliosides [30–32] have circulation lifetimes of up to several days, compared to several hours for conventional liposomes [33, 34] and other pharmaceutical microparticles [29]. The mechanism for the extended life of such liposomes is unknown. Possibly reduced opsonization of lipid bilayers can play a role in reduced phagocytosis of the modified liposomes. A method for coating magnetic particles with lipid bilayers has been reported by DeCuyper et al. [35, 36]. Ferrocolloids stabilized by fatty acids are used as a starting material and lipid bilayer from pre-formed small unilamellar liposomes is substituted for the fatty acid micelle. The procedure allows very high loads of ferromagnetic material to be incorporated into the resulting microparticles that have the structure of large unicellular liposomes. Further loading with a drug using liposome fusion is also possible [37].

The therapeutic potential of anticancer drugs is substantially limited by their high systemic toxicity. In attempts to avoid this disadvantage, there have been numerous efforts to deliver anticancer drugs specifically to a tumor. These efforts often used the principle of "recognition" molecules such as antibodies, lectins, desialylated glycoproteins, and autologous tumor lipids [38–40]. However, the modification imposed by a "recognition" molecule, or a bulky construct needed to combine a recognition portion with a drug substance always reduced the activity of the drug and/or its ability for extravasation into tissues, so that only very modest success has been achieved in this field. Another group of studies focused on microspheres as potential targetable drug carriers [41]; however, the yet unsolved problem of rapid reticuloendothelial clearance of such microspheres [27] puts the usefulness of this approach, in its present state, under question.

A different approach to drug targeting has been developed in the works by Yatvin et al. [42,43] and Huang et al. [44]. They used heat to induce rapid release of pharmaceuticals from thermosensitive liposomes composed of phospholipids having transition temperatures slightly above normal physiological temperature. Local hyperthermia, heating of the target area to a temperature of 42°–44° C., would cause the liposome lipids to "melt", and the liposomes flowing through the vascular bed of a hyperthermized area would rapidly release the entrapped drug into the surrounding medium. Since the drug is released in its intact form, the problems concerning drug extravasation and activity are avoided. So, in the approaches proposed by Yatvin and Huang, the targeted mode of drug delivery substantially depends on the ability to apply hyperthermia to the area of pathology in a targeted manner; unfortunately, none of the existing techniques of hyperthermia offers a general and satisfactory way to do so [10].

In the technique of magnetic resonance imaging (MRI), colloidal gamma ferric oxide has been used in human patients as a contrast enhancer [17]. The compound is virtually non-toxic and well tolerated when administered into the bloodstream. Its $LD_{50}$ in mice exceeds 2 g per kg [5]. No toxic effects were observed either upon acute (150 mg Fe/kg in 24 hours) or chronic administration in rats [14] or in human patient trials [15]. A principal magnetic property of importance for particles used in MRI imaging is the effect on the $T_2$ proton relaxation time. Contrast enhancement is increased by agents which decrease the $T_2$ relaxation time. (See, e.g., Cerdan, S., et al., (1989) Magnetic Resonance in Medicine, 12:151–163.)

SUMMARY OF THE INVENTION

The present invention provides novel superparamagnetic particles comprising gamma ferric oxide and a polymer, e.g., Dextran, or ficoll having exceptional magnetic properties. These properties include: (1) initial magnetic susceptibility greater than 0.7 EMU/gm iron/Gauss; (2) average particle magnetic moment greater than $1/\times 10^{-15}$ erg/Gauss; (3) specific power absorption rate (SAR) greater than 300 W/g iron, preferably greater than 350 W/gm iron; (4) saturation magnetization between 60 and 100 EMU/gm iron; (5) Dextran:iron ratio=0.1–0.5, preferably 0.2–0.4; (6) hydrodynamic diameter of 5–50 nm, preferably 15–30 nm (150–5000S, preferably 500–2500S); and (7) magnetic grain diameter=10–20 nm. In addition, the particles of the present invention lose significant magnetic properties in the presence of added citrate, in contrast to certain types of particles in the prior art reportedly stabilized by citrate. For example, the presence of citrate can result in a 50% decrease in SAR.

The particles of the invention can be prepared by a procedure described herein which incorporates several novel features.

The standard procedure of Molday includes the addition of aqueous ammonia to a solution containing dextran and iron salts. Surprisingly, we have found that the heating properties of the resulting particles increase if dextran or other suitable polymer is premixed with the necessary amount of aqueous ammonia, and the polymer-ammonia solution is added to the solution of iron salts (Table 2).

Furthermore, we have found that treatment of the reaction mixture with ultrasonic energy greatly improves the heating properties of the resulting ferroparticles (Table 2). The ultrasonic energy should be applied to the reaction mixture at least during the period when the solution of polymer and ammonia is being added (Table 3). While the use of ultrasonic treatment for preparation of magnetic and other colloids has been previously described, the unexpectedly beneficial effect of ultrasound applied during the formation and growth of polymer-magnetic iron oxide particles has not been previously reported. Tables 2 and 3 also show that in the absence of polymer, the ultrasonic treatment does not improve the heating properties of the particles.

Furthermore, in order to obtain optimum heating properties, we have discovered that the molecular weight of the polymer should be more than 40 kilodalton and, preferentially, more than 70 kilodalton (FIG. 1), and the concentration of polymer in the precipitant solution should be at least 30 weight parts of the polymer for each 100 volume parts of ammonia (FIG. 2).

We have also discovered that to obtain optimum heating properties of the ferrocolloid, the temperature should be maintained at 30°–40° C. during the polymer-ammonia addition/sonication step (FIG. 3), and 45°–70° C preferably 45°–55° C., thereafter (FIG. 4).

We have also found that the heating properties of dextran-coated magnetic iron oxide particles substantially depend on the particle size and may be further improved by selection of the particles having effective hydrodynamic diameters in the range of 5–50 nm, preferably 15–30 nm (FIG. 5). Therefore we introduced the size fractionation step in the method for particle preparation. We have used centrifugal fractionation, although any other method of size fractionation may be used. The centrifuge fractionation method employed here is explained in [26].

We have determined that magnetic particles prepared according to the invention and encapsulated in liposomes can have an extended lifetime in the bloodstream. Such particles largely escape the RES clearance which is the usual fate of injected magnetic particles. Such liposome encapsulated particles are termed ferroliposomes herein. In addition to acting as carriers for magnetic particles, the liposomes serve as vehicles for transport of incorporated therapeutic agents such as chemotherapeutic drugs. By proper choice of liposome transition temperature, the therapeutic agent can be released at the desired time and place by localized heating induced by application of an oscillating electromagnetic field. Such ferroliposomes can also be constructed with appropriate targeting molecules, as herein described. For example, antibodies to a tumor-specific antigen can be incorporated into a ferroliposome, making it possible to concentrate such ferroliposomes at the site of tumor cells. The ferroliposomes can therefore have dual utility: to cause local heating of the tumor tissue, and to release chemotherapeutic agents by "melting" of the liposome structure. The utility of ferroliposomes and magnetic particles of the invention is also appropriate for ex vivo treatments, for example in bone marrow transplant therapy. Finally, as noted, the magnetic particles of the invention, including ferroliposomes made according to the invention, are useful as MRI contrast-enhancement agents.

DETAILED OF THE INVENTION

The procedure for the preparation of polymer-coated, superparamagnetic colloidal iron oxides of the invention is performed in the following way.

First, the necessary amounts of ferric and ferrous salts, e.g., $FeCl_3\text{-}6H_2O$ and $FeCl_2\text{-}4H_2O$, are dissolved in water.

Second, the necessary amount of polymer, e.g., dextran, having average molecular weight of at least 40 kilodalton, and preferably 70–90 kilodalton, is dissolved in the concentrated aqueous solution of ammonia taken in 5- to 20-fold molar excess in respect to the iron salts.

Third, the dextran-ammonia solution is added slowly to the iron salt solution, the reaction mixture is continuously treated with ultrasonic energy during this step, and the reaction temperature is maintained at 30°–40° C.

Fourth, the ultrasound treatment is stopped, and the product is heat-treated at 40°–70° C. preferably at 45°–55° C., for at least 10 min.

Then the acidity of the product is adjusted to pH 5.5–6.5, the grossly aggregated material is removed by low speed (600–1200 g) centrifugation, and the ferrocolloid is purified from the salts, low molecular impurities, and unbound dextran using one or more of the known techniques, such as dialysis, high speed centrifugation, high-gradient magnetic separation, or gel filtration.

Finally, the ferrocolloid is fractionated according to the particle size using one or more of the known methods, such as microfiltration, centrifugation, gel-filtration of highly porous matrices, and the like, and the fraction having the highest specific heating rate (Watts/mg of iron) under the given RF EM field parameters is selected.

Although adherence to the general protocol just described, or as described in the examples, yields ferrocolloids having the defined magnetic properties of the invention, it will be understood that other processes and variations of the described process can yield the magnetic particles of the invention. The properties of SAR, initial magnetic susceptibility, magnetic moment and saturation magnetization are measurable by standard protocols which can be carried out by those of ordinary skill in the art.

The ferrocolloids of the invention are of superparamagnetic iron oxide particles associated with molecules of a polymer, e.g., unmodified dextran, and should be free from potentially toxic impurities, such as fatty acids and synthetic surfactants. Suitable polymers must be biocompatible, soluble under the reaction conditions, and include, for example, ficoll, chondroitin sulfate and dextran sulfate, as well as unmodified dextran. Tests of a variety of polymers were conducted, the results of which are summarized at Table 9. In each test, the polymers were pre-mixed with ammonia as provided by our standard procedure, then added to the Fe salts. These ferrocolloids are indefinitely stable in the presence of physiological concentrations of salts and pass through microfilters conventionally used for sterilization. They can be administered to the desired areas in the patient's body using any suitable technique known in the art. Examples of such administration methods are: intratumoral, peritumoral, or intravascular administration, intravenous, intraperitoneal, subcutaneous, or intrathecal injections, and superficial applications. The ferrocolloid particles can be directed to the areas of pathology, e.g., tumors, by combining the particles with tumor-seeking agents, examples of which are: tumor-specific antibodies, porphyrins, liposomes, lipoproteins, lectins, and tumor surface receptor-binding agents. Such combination can be by chemical bond or via physical interaction, such as, for example, absorption or lipid bilayer coating. Due to the strong magnetism of the particles, their confinement in the treatment area can be assisted by an applied static magnetic field. The described particles can be associated with other treatment agents, such as pharmaceuticals, or radioisotopes, to perform concurrent treatment by heat and the associated therapeutic agent, or to assist in the release of the associated agent into the treatment area. The particles can be further associated with agents that would favor their accumulation in the treatment area, such as ferritin, or RES-masking agents like monosialogangliosides or polyethyleneglycol. Because of their unique magnetic properties, the targeted delivery of the superparamagnetic particles produced according to the present invention is facilitated by the fact that the necessary amount of magnetic material to be delivered to the treatment area is at least an order of magnitude lower than that for any other previously reported ferromagnetic material, so that the necessary targeting may be achieved by targeting methods of customary, rather than exceptional, effectiveness. In effect, the particles of the present invention permit application of hyperthermia treatments as a practical matter in a variety of therapeutic contexts.

A panel of ferrocolloids was prepared using the above-described inventive procedure and tested for their specific power absorption rates in fields of various frequencies and amplitudes, as well as for their ability to cause tumor heating and hyperthermia-induced tumor cell killing in cell cultures.

We have estimated the amounts of magnetic materials, prepared according to the present invention, as well as those reported in [11] and [16] (selected as the best of previously reported ones), required for the effective heating of human tumor. We followed the theoretical analysis of heat dissipation during hyperthermia described in [24] and [25]. The results of calculations given in Table 4 suggest that concentration of 0.5 to 1 mg of iron/g of tumor would be sufficient for therapeutic tumor heating, as opposed to at least an order of magnitude higher values for the previously reported materials.

We have studied in vivo tumor heating properties of the ferrocolloids prepared according to the present invention. Human lung cancer xenografts were grown subcutaneously in the flanks of nude (nu/nu) mice to the size of 1.5–2 cm. Dextran-coated magnetic iron oxide was prepared according to the procedure described in Example 1 below, adjusted to physiological sodium chloride concentration by adding 1/10 volume of 10×phosphate buffered saline, and sterilized by filtration through 0.2 μm filter. The resulting solution with the concentration of iron 30.5 mg/ml was injected intratumorally into mice anesthetized with 60 mg/kg Phenobarbital intraperitoneally. The injections were made in 3 μl portions using a Hamilton microsyringe to obtain uniform distribution of the ferrocolloid in the tumor. Total amount of iron injected varied in the range of 0.4–2 mg/g of tumor weight. A fiberoptic thermometer probe of a Luxtron TM Fluoroptic thermometer was inserted centrally into a tumor, and another probe was used to monitor rectal temperature of the animal. The animals were subjected to the oscillating electromagnetic field at the frequency of 847 kHz and amplitudes of 75–90 Oe, and the temperature of the tumor and the rectal temperature were monitored. There was no detectable increase in the body temperature of the animals without tumors, or in the tumors without injection of the ferrocolloid particles. The results of tumor heating experiments are presented in Table 5. These results indicate that tumor tissue concentrations of ferrocolloid particles prepared according to the invention provide a therapeutically significant increase in the tumor temperature at concentrations equal to, or below than, 1 mg/g of tissue, which is in good agreement with the theoretical evaluations given in Table 4. These results confirm that the ferromagnetic colloids produced according to the present invention provide substantially better heating than other, previously known types of similar materials.

We established at least two independent material properties of the particles that have excellent correlation with the heating quality. These properties are (1) initial magnetic susceptibility of the particles in solution ($X_i$), and (2) the average particle magnetic moment ($\mu_{av}$). Both properties were determined from the static magnetization curves obtained for particles in solution at 5–30 mg Fe/ml, T=290K using SQUID TM magnetometer in the range of 0–10000 Oersted. We have measured 23 samples including 8 batches prepared according to our invention (using Dextran 70, Dextran 250, and Ficoll 400 as polymers). Other samples were particles prepared according to Molday, SangyoMeito, AMI (U.S. Pat. No. 4,827,945 Paragraph 7.10) prepared without polymer or with a fatty acid stabilizer, and particles prepared using our procedure with omissions of certain steps or with sub-optimal process parameters resulting in poorer heating quality. The results are given at FIGS. 6–8. Particles prepared according to our invention are given as black circles, the other ones are white circles. All our particles group together beautifully in the upper right corner of both graphs and are clearly separated from all other particles. If we establish the qualifying value for heat production as >300 W/gm Fe (at 1 MHz, 100 Oersted field) preferably >350 W/g Fe, we can establish from these graphs also the corresponding qualifying values of $X_i \geq 0.75$ emu/Gauss/g Fe and $\mu_{av} \geq 10^{-15}$ erg/Gauss (these values are marked on FIG. 1 by dotted lines). It is an unexpected correlation that we cannot trivially derive from the common knowledge of magnetic physics. In fact, at this moment we do not have any clear theoretical explanation to this correlation.

On the basis of this finding we suggest the following list of qualifying properties to describe our particles:

1. The particles are magnetic iron oxide particles associated with a polymer (polysaccharide).
2. The particles are superparamagnetic, i.e., possess negligible coercivity.
3. The particles form a suspension in a physiologically acceptable, water-based medium, and this suspension is stable against precipitation under gravity.
4. The particles have average magnetic moment of at least about $10^{-15}$ erg/Gauss or more, up to about $1.6 \times 10^{-15}$ erg/Gauss, as derived from the measurements of static magnetization curve at 5–30 mg Fe/ml, temperature of about 290K, and in the range of 0–10000 Oersted.
5. The particles have initial magnetic susceptibility of at least about 0.75 EMU/Gauss/g Fe or more as measured in a water-based solution at 5–30 mg Fe/ml and temperature about 290K with applied magnetic field H=50 Gauss. Values of initial magnetic susceptibility up to 1.1–1.2 EMU/Gauss/g Fe are obtainable according to the invention.
6. The particles have specific power absorption rate (SAR) of at least 300, preferably more than 350 W/g Fe as measured in a water-based medium in an electromagnetic field having the frequency of 1 MHz and peak-to-zero amplitude of 100 Oersted. Particles having SAR up to 600 W/g Fe are obtainable according to the invention.
7. The particle hydrodynamic size lies predominantly in the range characterized by sedimentation constant between 150 and 5000 S, preferably between 500 and 2500 S, as determined by centrifugal fractionation in dilute aqueous solution at the temperature of about 290K.

In addition, we have obtained data suggesting that the presence of citrate, at a concentration used to stabilize prior art particles, substantially reduces the particle heating quality, as well as the particle average magnetic moment. See Table 6. The particles should therefore be maintained essentially citrate-free, by which is meant that citrates per se 15 should not be added to particle preparations that are meant to be stored more than a few hours.

We have also studied batch-to-batch variations in particle quality using five different batches of dextran with mol. weights in the range of 70–76 KDa (from Sigma), and one batch of Dextran 256 KDa. The variations in the yield of particles and SAR were as shown in Table 7.

The iron of the particles is composed essentially entirely of superparamegnetic $\gamma$-Fe$_2$O$_3$. X-ray diffraction of high-SAR particles is shown in FIG. 11, confirming the $\gamma$-Fe$_2$O$_3$ structure of the particles. Particles of low SAR, prepared by a suboptimal variant of the method of preparation described herein yield an X-ray pattern shown in FIG. 12. FIG. 13 shows a magnetization curve of high-SAR particles, indicating lack of hysteresis in confirmation of the superparamagnetic character of the particles.

Dextran-to-iron ratio was determined as follows:

0.5-ml aliquots of iron oxide colloids (iron concentration, 5–30 mg Fe/ml) were applied onto an Econo-Pak TM column (Bio-Rad, USA) packed with Sephacryl TM S-400HR (Pharmacia, Sweden) and eluted with 0.05M sodium-acetate buffer, pH 6.0. The colored fraction appearing near the void volume was collected and analyzed for iron and dextran content. The purpose of the gel-chromatography step was to separate unbound dextran from the particles.

Iron concentration in the sample purified by gel-chromatography as above was determined by ortho-phenanthroline method as described (A. I. Vogel. A Text-Book of Quantitative Analysis, 3rd Ed., Wiley, New York, 1961, p. 786-787).

Dextran concentration was determined by phenol-sulfuric acid method as described (M. Dubois, K. A. Gilles, J. K. Hamilton, P. A. Rebers, F. Smith, Anal. Chem 28(3):350-356, 1956). Since it was found that the presence of iron affects the standard curve, standard curves were obtained for dextran in the presence of 2, 5, 10, 25, and 50 µg of Fe per aliquot of sample.

Dextran-to-iron ratio was calculated by dividing the concentration of dextran in the sample by that of iron. The effect of dextran:iron ratio on the SAR of resulting particles is shown in FIG. 9.

Determination of initial susceptibility of iron oxide colloids and average magnetic moment of the particles was performed as follows:

1. Obtaining magnetization curves.

Magnetization curves of iron oxide colloids (5-30 mg Fe/ml) were obtained using MPMS-2 SQUID TM magnetometer (Quantum Design, USA) at 290K in the range of 0-10,000 Oersted. Samples (0.25 ml) were placed in a sealed cylindrical cell with i.d. 4 mm, height 10 mm. The magnetization values were normalized to the unit mass of iron in the sample.

2. Determination of the initial susceptibility,

The values of magnetization (M), in EMU/g Fe, obtained at 0, 5, 10, 15, 20, 25, and 30 Oersted, were plotted against the field (H), and approximated using first-order polynomial (linear) regression. The initial susceptibility of the sample was taken as a gradient of the regression line. Correlation coefficients obtained were better than 0,998.

3. Determination of the saturation magnetization and the average magnetic moment of the iron oxide colloid particles.

The values of M, obtained at 1000, 1400, 2000, 3000, 5000, and 10,000 Oersted were plotted against the reverse field (1/H), and approximated with second-order polynomial regression. Correlation coefficients were always better than 0,998. The saturation magnetization was found as the intercept of the regression line and the ordinate axis.

Average magnetic moment of particles was calculated from the initial susceptibility and saturation magnetization according to the formula known for diluted superparamagnetic ferrofluids (R. W. Chantrell, J. Popplewell, S. W. Charles, IEEE Trans. Magn., MAG-4(5):975-977, 1978):

$$X_i = \frac{M_s}{3kT} \int_0^{X_{max}} \mu(x)f(x)dx = \mu a_{av}\frac{M_s}{3kT}$$

where $X_i$ is initial susceptibility, $M_s$ is saturation magnetization, T—absolute temperature, $\mu$—magnetic moment of a particle, f(x)—particle size distribution function, $\mu_{av}$—average particle magnetic moment, and $\kappa$ is Boltzmann's constant. x—particle size.

Determination of proton $T_2$ relaxation in the presence of superparamagnetic iron oxides was carried out as follows:

Magnetic iron oxide colloids were diluted serially (from 0 to 30 µg Fe/ml) with distilled water. A rack of 50 samples with 15 ml/tube was placed inside a head coil and magnetic resonance images were measured with a GE Signa, 1.5T Model, at 63,85 MHz, equipped with version 5.2 software. Spin echo at SE 2000/20,40,60, and 80 ms sequences were scanned. Digitized intensities of each sample were recorded and $T_2$ was determined from curves by plotting Log (intensities) vs. echo times (ms). $T_2$ of water in the presence of various magnetic colloids was plotted against iron concentrations. The results are shown in FIG. 9. Curves labeled as filled, black triangles or open squares were the results obtained from magnetic particles of the present invention. The curve indicated by open triangles was the result obtained with particles precipitated without polymer, while particles precipitated with insufficient polymer yielded the curve indicated by solid circles. Open circles indicated the data obtained with particles prepared according to Cerdan, S., et al.

The appropriate choice of the method for the synthesis of colloidal ferromagnetics protected from recognition by the cells of mononuclear phagocyting system is useful to expand the range of application of ferrocolloids of the invention. We synthesize colloidal (nanometer size) iron oxide with the increased radio frequency-induced heat production using the procedure of the invention. We employ the method of Reimers and Khalafalla [69] to introduce fatty acid coating onto the surface of the ferrocolloid particles. We use lauric acid with trace quantities of $^{14}C$-labeled lauric acid in the diluted aqueous ammonia to quantitatively monitor the amount of laurate associated with the colloid. Further we employ the lipid substitution method by De Cuyper and Joniau [35,68] to substitute a phospholipid bilayer for the lauric acid coating on the surface of the ferrocolloid particles. In this method, two crucial innovations are introduced. First, we include a special phospholipid derivative, polyethylene glycol-conjugated distearoyl phosphatidylethanolamine (PEG-DSPE) into the lipid bilayer coating of a ferrocolloid. This derivative will be synthesized by us using the described procedure [70]. This phospholipid derivative has proven very efficient for increasing the circulation lifetimes of liposomes. The second innovation deals with the problem of hydrophilic chains of polyethylene glycol which can interfere with the interaction between phospholipid molecules and iron oxide groups essential for the substitution. To avoid this interference and to increase the yield of polyethylene glycol groups at the surface of ferrocolloid particle, we take advantage of the fact that the lipid substitution process has two stages [35,68]: the first, fast stage when phospholipid monolayer is formed on the surface of a laurate-stabilized ferrocolloid incubated in the presence of phospholipid bilayer liposomes, followed by a considerably slower stage when a second phospholipid layer is built to complete the bilayer structure (hours). Therefore we first briefly incubate the laurate-coated ferrocolloid with the liposomes of a phospholipid having strong affinity to iron oxide, e.g., distearoylphosphatidyglycerol (DSPC); then, we separate the partially substituted ferrocolloid from excess micellar lauric acid by size exclusion chromatography and/or high gradient magnetic separation, and further incubate it in the presence of PEG-DSPE-containing liposomes to build up the second phospholipid layer with the introduced polyethylene glycol groups. The course of substitution is monitored by radioactive tracer method using $^{14}C$ lauric acid. The same synthetic procedure is also employed to obtain ferroliposomes bearing cancer cell-specific antibody fragments.

Large oligolamellar DSPG and PEG-DSPE/hydrogenated egg phophatidylcholine/cholesterol liposomes to be used as a phospholipid source for the above substitution reactions are prepared by a membrane extrusion technique [50] as it provides less vigorous treatment of phospholipids compared with conventional sonication, solvent injection and reverse evaporation techniques.

Finally ferroliposomes are separated from the excess phospholipid by high gradient magnet separation, extensively dialyzed against physiological saline solution, sterilized by microfiltration and stored at +4° C. for further studies.

The ferroliposomes are characterized by the following parameters: lipid composition, iron content, ultrastructure and particle size distribution, amount of heat produced in the radiofrequency electromagnetic field, in vitro cytotoxicity, and stability in the presence of serum.

Iron content of the ferroliposomes is determined using a colorimetric assay [75] after digestion of the sample with sulfuric acid. Total phospholipid content of the ferroliposomes is determined by phosphorus assay in the samples digested with sulfuric acid in the presence of hydrogen peroxide. Phospholipid composition is determined by TLC of the chloroform extracts of ferroliposome samples using silica plates and methanol-chloroform-water solvent systems as described [77]. Ultrastructure and size distribution of the ferroliposomes are determined by electron microscopy. Specifically, the ferroliposomes are applied onto collodion-covered grids reinforced with carbon and negatively contrasted with uranyl acetate and phosphotungstic acid. Since the ferromagnetic substance is electron dense itself, the comparison of contrasted and non-contrasted specimens provides information about overall size of ferroliposomes, the size and shape of the lipid component, and the inside distribution of the ferromagnetic substance. Size distributions of ferroliposomes are obtained from direct measurements of electron microscopic images.

It is important to ensure that the change of lipid coating does not affect the heat-producing properties of the particles exposed to radiofrequency electromagnetic fields. Therefore, we determine specific heat production of ferroliposomes using our standard procedures described herein.

Although colloidal magnetic iron oxides have displayed extremely low toxicity in animals [76], the presence of lipid components in combination with iron oxide brings about the need to study the cytotoxicity of ferroliposomes. Various human cell lines: A549 (lung adenocarcinomas), ZR75 (breast tumors), SHP77 (small cell lung carcinomas), and FS24 (normal skin fibroblasts) are grown in RPMI 740 medium supplemented with 10% fetal calf serum in the presence of various amounts of ferroliposomes. Cell growth and viability are determined by our routine ($^3$H)thymidine incorporation assay and the trypan blue exclusion assay.

Radiolabeled ferroliposomes are used in the subsequent in vivo (biodistribution and blood clearance) studies and in vitro cell binding assays. For in vivo studies we use the double label method to follow the biodistribution of lipid and iron oxide components of the ferroliposomes separately. The first label, $^{51}$Cr, is introduced into the ferromagnetic component at the stage of synthesis of magnetic colloidal iron oxide, by isomorphic coprecipitation of $^{51}$Cr$^{3+}$ in the mixture of ferric and ferrous salt. The $^{51}$Cr label provides better environmental protection, less hazard, and is less expensive than the $^{59}$Fe label. The second label, $^{125}$I, is introduced into the lipid bilayer in the form of a labeled phospholipid derivative. We prepare this derivative by reaction of distearoylphosphatidylethanolamine with the radioiodinated Bolton-Hunter reagent. Both compounds are commercially available. The $^{125}$I-labeled phospholipid is introduced at the lipid substitution stage by addition of the $^{125}$I-phospholipid to the lipid mixture for preparation of liposomes. Another advantage of this double label system is that we are able to determine both isotopes in the same sample using different energy windows and therefore to obtain the data for the distribution of the lipid and ferromagnetic component in the same experiment. It reduces by twofold the number of animals and the amount of time required for a biodistribution study. The same double label is used also in cell binding assays and in vivo studies of ferroliposomes modified with cell-specific antibodies.

Briefly, ferroliposomes suspended in physiological saline are injected in the tail vein of 2-3 month old CD-1 mice (Charles River) under mild anesthesia. At 1, 4, 12, 24 and 48 hours after injection the animals are anesthetized with ether and totally bled through ventricular puncture. The blood is collected, sampled, and the rest is centrifuged to obtain plasma samples. The carcasses are completely dissected, organs and tissue samples excised, weighed, and the radioactivity of $^{51}$Cr and $^{125}$I determined in each sample. The accumulation of radiolabeled materials is expressed as percent of injected dose per gram of tissue for the iron oxide and lipid separately. Following our conventional procedure, we analyze at least the following samples: blood, plasma, liver, spleen, lungs, kidney, heart, brain, lymph nodes (inguinal plus retroperitoneal), small and large intestine, muscle, skin, bone marrow, and hard bone tissue. Blood volume and correction factors for the blood content of various tissues are made as in prior studies [71,72]. To facilitate the analysis of tissue distribution data we combine the organs and tissues into the following groups: blood, plasma, liver-spleen, carcass-skin, lungs, lymph nodes, bone marrow, and other tissues. In order to reduce the required number of animals, we use one animal per time point for preliminary screening of ferroliposome preparations; however, for the preparations showing circulation lifetimes more than 4-6 hours and decreased liver/spleen uptake, the experiment is repeated to obtain at least three measurements for each time point. On the basis of the data obtained at this step, we select the formulation of ferroliposomes that displays the lowest reticuloendothelial uptake to be used in subsequent work.

It has been noticed that PEG-modified liposomes injected iv. into animals with implanted malignant tumors accumulate in tumor tissues in the quantities compared to that of liver and spleen [66,67,11]. We use nude mice with implanted human tumors to demonstrate that the same phenomenon can be observed for the PEG-ferroliposome formulation(s) developed at the previous stage. Eight to ten week old athymic BALB/c mice are inoculated s.c. into the hind leg with $(1-5) \times 10^6$ tumor cells from human cancer cell lines A-549 (lung adenocarcinoma), ZR75 (breast carcinoma), and SHP77 (small cell lung carcinomas). After 2-3 weeks from inoculation when the tumor implants usually measure about 0.5 to 1 cm in diameter, the animals are injected with various doses of the previously selected ferroliposomes and analyzed as described above, with the following differences:

1. time points of 6, 24, 48 and 96 hours are chosen;
2. along with the other tissues as described above, tumor tissue is excised, weighed, and the content of the ferromagnetic iron oxide and the liposome lipid are determined from radioactivity in the similar manner.

The biodistribution data obtained at this time are used to determine the optimal injection dosage of ferroliposomes and evaluate the parameters of radiofrequency electromagnetic field necessary for development of hyperthermia in the tumor tissue.

Numerous studies have been performed in attempts to confine magnetic pharmaceutical microparticles in the tumor by an external magnet [64,65,27]. The major reason for failure of these attempts has been rapid clearance of the microparticles from circulation by reticuloendothelial cells. Since PEG-ferroliposomes are designed with the purpose to avoid rapid blood clearance, it seems appropriate to determine the extent of concentration of the ferroliposomes in the tumor by applying an external magnet to the tumor area. The experimental scheme is similar to that of the biodistribution experiment just described; in addition, permanent magnet of neodymium-iron-boron alloy (0.6 Tesla at the surface; cylindrical 0.5"×0.541) is placed at the skin projection of tumor prior to the injection of ferroliposomes. The magnet is held in place by adhesive tape and removed 2-6 hours after the injection. The amount of iron oxide accumulated in the tumor is multiplied by previously determined specific heat production rates of the ferroliposomes to give an estimate for the parameters of radiofrequency field required for efficient hyperthermia of the tissue.

Following biodistribution studies showing accumulation of ferroliposomes in the tumor tissue, we perform ultrastructural studies of the tumors with absorbed ferroliposomes to understand the fine distribution patterns of the ferromagnetic material in the tissue. This information helps to understand the heat distribution in the tumor exposed to a radiofrequency field in subsequent studies. Ferric oxide is an intensely colored, electron dense material, easily recognizable at the light and electron microscopy pictures. Freshly excised tumor tissue is fixed, stained, embedded in paraffin and examined through light microscope to obtain a gross picture of the ferric oxide distribution inside the tumor. The details of interaction between absorbed ferroliposomes and tumor cells are studied by electron microscopy of the ultrathin sections from the tumor tissue fixed with osmium tetroxide and embedded in Epon. Samples for light and electron microscopy are prepared by Department of Pathology, University of Colorado Health Sciences Center, using their routine procedures. We also study samples of principal reticuloendothelial organs (liver, spleen, bone marrow, lymph nodes), lungs, and kidneys. This study allows for comparison of the mechanisms responsible for the accumulation of ferroliposomes in different tissues.

In order to increase affinity of ferroliposomes to cancer cells we shall adopt the approach of combining the ferroliposomes with antibodies against cancer cell surface antigens. Generally the antigen binding chains are anchored to the lipid bilayer surrounding the ferromagnetic core of a ferroliposome through a covalently attached hydrophobic residue. Similar techniques are described [78]. However, we observe three important conditions. First, the presence of Fc fragment of an antibody molecule on the surface of a PEG-ferroliposome increases its chance to be phagocytosed through a mechanism mediated by mononuclear Fc-receptors. Second, the position of a hydrophobic anchor must ensure the correct, outward orientation of antigen binding sites. Third, the chemical bond between the antigen binding fragment and the hydrophobic "anchor" chain (and, consequently, the ferroliposome) must be stable in the presence of common components of blood plasma. To satisfy these conditions, we employ the following scheme for the synthesis of PEG-ferroliposomes with the antibody-derived affinity to cancer cells:

(a) Monoclonal antibodies against cancer cell surface antigen are digested by pepsin, and $F(ab)_2{}^1$ fragments isolated. Specifically, we use KC4G3 murine $IgG_3$ monoclonal antibody (Coulter) reactive to 400K surface glycoprotein produced by various human adenocarcinomas [74,79] and the $F(ab)^2{}2$ is prepared using a commercial reagent kit (Pierce).

(b) Saturated long-chain phophatidylethanolamine is modified by a bifunctional crosslinking reagent to introduce a thiol-binding group. We use distearoylphosphatidylethanolamine (Avanti PolarLipids), and modify it with succinimidyl 4 (-p-maleimidophenyl)butyrate (Pierce) in benzene in the presence of triethylamine as described [70]. The resulting phospholipid derivative, MPB-DSPE carries a thiol-reactive maleimide group at the hydrophilic "head" of its molecule.

(c) $F(ab)^1 2$ fragments are reduced by mercaptoethylamine to give $Fab^1$ fragments. $Fab^1$ fragments are purified by gel-filtration using oxygen-free buffer and immediately reacted with MPB-DSPE solubilized by a dialyzable detergent octylglycoside. Since the only available thiol groups are at the hinge region of $Fab^1$ fragments, the antigen binding sites remain intact. Unreacted maleimide groups are destroyed by mild alkaline treatment (pH 8-8.5). There is no need to separate unreacted $Fab^1$ fragments at this step since they do integrate into liposomal membrane during further procedures.

(d) PEG-derivatized DSPE, cholesterol, and DSPC or hydrogenated egg phosphatidylcholine (HEPC) are added to the reaction mixture to the proportion established in the previous section.

(e) The reaction mixture is dialyzed against buffer to achieve formation of small unilamellar liposomes (detergent dialysis liposomes) as described [7,374]. These liposomes incorporate both PEG groups and Fab-groups oriented outward from the lipid bilayer. The liposomes are separated from unreacted $Fab^1$ and residual octylglycoside by gel filtration using Sephacryl S-400 (Pharmacia).

(f) The liposomes obtained at the prior step are used to complete a bilayer formation on the surface of ferrocolloid particles as described in the previous section. The modified ferroliposomes—immunoferroliposomes—are purified from unreacted PEG -and $Fab^1$ -DSPE liposomes by high gradient magnetic separation as described herein, resuspended in physiological buffer, sterilized by filtration, characterized by their size distribution, lipid and iron content as described in the previous sections, and stored at 4° C. for further studies.

The incorporation of antibody fragments into desirable products throughout the above procedure is monitored by radioactivity using $^{125}$I-labeled antibody. We label the initial KC4G3 antibody by the IodoGen method (Pierce).

Immunoreactivity and binding specificity of ferroimmunoliposomes is compared to that of intact KC4G3 in the two types of assays. First, we perform standard immunobead assay (Coulter Immunology). Second, we study in vitro binding of immunoferroliposomes to the antigen producing human cancer cells—A549 (adenocarcinoma), ZR75 (breast carcinoma), and H460 (large cell lung carcinoma), as well as non-antigen producing cells—FS24 (human skin fibroblasts) and HM-5 (EBV transformed human B cells). All these cell lines are routinely maintained in our laboratory. We use a standard competition binding study and direct binding study using $^{51}$Cr-labeled immunoferroliposomes and $^{125}$I-labeled KC4G3 prepared as described.

Biodistribution and blood clearance of immunoferroliposomes are performed essentially as described for ferroliposomes. Additionally, we follow Fab$^1$ fragments along with the ferric oxide component using immunoferroliposomes with $^{125}$I-labeled Fab$^1$ and non-labeled lipid.

To evaluate the potential of antibody targeting for improvement of ferric oxide uptake by a tumor, ferric oxide colloids designed for use in this study provide a temperature increase of approx. 5°-6° C./min in the electromagnetic field at 1 MHz and 100 Gs (which still produces negligible background heating of a tissue) at a tissue iron concentration of about 0.1%. Therefore the accumulation of iron in the tumor exceeding 0.02–0.03% is sufficient to produce enough heat in the targeted area with our RF induction heating instrumentation. To evaluate the RF field parameters for further work, we study the RF-induced heating of tumors excised from animals after administration of (immuno)ferroliposomes. The tumors are placed in plastic vials containing physiological saline and inserted into the inductor coils currently used by us for in vitro heat production studies. Our present set of air-cooled inductor coils with Faraday shield is in the range of 0.15–1.1 MHz and provides the field with peak strength up to 160 Gs. Non-conductive 0.8 mm thermoprobe (Luxtron TM Fluoroptic thermometer) are inserted in the central part of the tumor specimen. Another probe is placed into the saline solution surrounding the tumor specimen. Temperature vs. time curves are obtained for RF fields of various frequency and field strength. The optimum field parameters for the further in vivo experiments are selected on the basis of these results.

Radiofrequency field generation. The work with larger animals (rats) requires the construction of an electronic setup suitable for generation of radiofrequency electromagnetic field with the necessary parameters. The inductor is a water-cooled coil with the inner diameter of 3.5 inches made of a copper tubing of appropriate gauge and mounted on Teflon supports. The final geometry of the coil is selected to match the requirements for frequency and field strength. Inside the coil, a cylindrical Faraday shield is mounted to reduce the electric vector of the field and therefore the non-specific heating by dielectric losses. The coil constitutes part of a resonant tank with parallel matching to couple the tank to 50 Ohm output impedance of the high frequency power amplifier (700A1, Amplifier Research). Field strength inside the coil is calculated from coil geometry and coil voltage measurements. The inductor coil and other elements of a resonant tank are placed inside a grounded cage to reduce the field outside the working area to the levels acceptable by occupational safety and FCC regulations. Other components of the electronic system are the same as described herein.

Thermometry. To avoid interferences caused by inductive heating of conductive elements, the temperature sensors must be totally non-conductive. Currently we use Luxtron TM Fluoroptic fiberoptic electronic thermometers with totally non-conductive, sterilizable thermoprobe 0.9 mm in diameter. For some studies, however, we also need a multichannel variant of this instrument that allows simultaneous monitoring of temperatures at least in the following sites: center of the tumor; tumor periphery; normal tissues surrounding the tumor; subcutaneous space at the uninvolved area; rectum.

The animals used for tumor heating studies are five-week old nude rats (Rowett) inoculated s.c. into hind leg with $10^7$ tumor cells of the chosen lines. The tumor implants usually reach 0.5–1 cm in size after 2–3 weeks. Initially the series of acute experiments is designed to determine the temperature distributions in the tumor and surrounding tissue and to develop the scheme for maintaining the desired temperature in the tumor for a given period of time. To determine the temperature patterns, anesthetized animals are placed in a non-conductive support and catheters inserted according to the scheme described in the thermometry section. The hind part of the animal is placed into the inductor, and the temperature vs. time curves obtained with the previously estimated field parameters. This experiment shows (a) the heating time necessary to achieve the temperature of 42°–44° C. required for hyperthermia treatment [59–63]; (b) the effect of heat washout with blood flow in the tumor by comparing the heating rate with that of in vitro heating experiment; and (c) the uniformity of heating throughout the tumor mass. The field is adjusted in repetitive experimental runs to optimize the above parameters. We perform sufficient repetitions to achieve reliable and reproducible temperature increase in the tumors. Next, to maintain the tumor temperature, we use the pulse-modulated field principle and the power controller described herein. Again, the adjustment of temperature offset, pulse frequency and pulse start temperature is needed to work out the protocol for maintaining the intratumor temperature with the accuracy of at least ±0.3° C. These adjustments require at least ten experimental runs initially. It is important to normalize the temperature patterns to the actual amount of heat-producing ferric oxide accumulated in the tumor tissue. Therefore after each experimental run the animal is sacrificed by overdose of the anesthetic, the tumor and adjacent normal tissue excised, tumor weighed, and iron concentration is colorimetrically determined by o-phenanthroline reaction after mineralization of the tissue samples. From these studies it is possible to work out a protocol for maintaining the preset temperature in the range of 42°–44° C. for 30°–60° minutes. In experiments designed to verify the reproducibility of heating patterns, we also examine the excised tumors (and surrounding non-tumorous tissues) for acute histopathological changes induced by ferroliposome-mediated heating of the tissues.

We have constructed a series of induction coils and assembled the electronic scheme for generating electromagnetic fields in the frequency range 0.15–1.1 MHz and peak field strength up to 200 Gauss. The coils are 0.5"×0.5" in size, air-cooled, and equipped with a Faraday shield to reduce the effect of electrostatic component on the sample. Radiofrequency power is fed from 700 W power amplifier (Amplifier Research 700A1) into a resonant tank, part of which is the inductor coil. The load is matched to 50 Ohm; the amplifier is connected to a quartz-stabilized 11 MHz sine wave generator (Wavetek Model 22). Field strength is determined from the coil voltage reading by oscilloscope. Temperature of the sample is monitored with the accuracy ±0.1° C. with Luxtron TM Fluoroptic electronic thermometer using a non-conductive fiberoptic probe. This assembly proved efficient in our cell culture studies on ferromagnetic hyperthermia [11,16].

We synthesized a panel of colloidal ferric oxides using alkaline precipitation technique modified after [69]. The ferrocolloids were compared by the heat-producing power (P) in the fields of different strength (H), and frequency (f). We found that all ferrocolloids satisfied the equation: $P = k \cdot F \cdot H2$, where k is a constant for a given preparation. The production of heat by ferrocolloids synthesized according to our procedure was 3–5 times higher than that of commercially available preparations (Table 1). It is important that heating of a physiological saline buffer exposed to the same fields was below the limit of detection.

Since the specificity of our proposed drug targeting method substantially depends on the site-specific application of the RF EM field, we studied the effect of sample position on the heating rate of a ferrocolloid. Practically no heating was observed for the sample outside the induction coil, while inside the coil the heating rate varied only slightly; thus, efficient heating of a ferrocolloid, i.e. expected release of a ferroliposome-entrapped drug, is indeed confined within an area inside the inductor coil.

We prepared a series of thermosensitive liposomes from dipalmitoylphosphatidylcholine (DPPC) and dipalmitoylphosphatidylglycerol (DPPG) (1:0.05 molar ratio) using sonication technique. We also studied the temperature-induced release of a solute from the DPPC-DPPG liposomes using indicator 5(6)-Carboxyfluorescein (CF). Fluorescence of 50mM CF entrapped into liposomes is more than 95% quenched by concentration self-quenching; the released indicator becomes strongly diluted and fluoresces proportionally to its concentration [45]. The effect of temperature on the release of CF from the liposomes was studied by monitoring the sample fluorescence in the thermostatted cell placed in the Aminco SLM 8000 fluorometer. Our findings were similar to the published data [42]. We also prepared two samples of ferroliposomes using a commercial ferrocolloid (EMG 1111, Ferrofluidics Corp.) incorporated into the lipid phase of the liposomes (0.2 mg of iron per 1 mg of lipid) as described below. Ferroliposomes were prepared by sonication at 55° C. and separated from unbound CF by Sephadex G-25 gel filtration. The ferroliposomes had the same solute release characteristics and responsiveness to heating as regular DPPC-DPPG liposomes; the efficiency of temperature-induced release of CF from ferroliposomes increased in the presence of serum (FCS) as it did for the liposomes without ferrocolloid.

1. Synthesis of thermosensitive ferroliposomes.
  a. nipids. The liposomes are prepared using dipalmitoylphosphatidylcholine (DPPC; Tc 41° C.) and distearoylphosphatidylcholine (DSPC; Tc 54° C.), so that any desirable Tc in the range of 41°–54° C. can be achieved by combination of these two components. The use of saturated phospholipids also reduces oxidation damage which is likely in the presence of iron [80] and therefore improves the storage stability of the liposomes. In order to increase aggregation stability of the liposomes we partially substitute dipalmitoylphosphatidylglycerol (DPPG) for DPPC in the amount that gives about 10 mol% of total lipid. DPPG (Tc 50° C.) endows the liposomes with additional negative charge that prevents aggregation.

b. synthesis of ferrocolloid and its incorporation into the lipid. Efficient incorporation of both ferrocolloids and drug substances into liposomes is a challenging task. If ferro liposomes are prepared by simple entrapment of hydrated ferrocolloids, the efficiency of entrapment, i.e. the ferromagnetic loading of liposomes is very low; besides, it is difficult to get rid of unincorporated ferrocolloid [46]. The lipid displacement method [35] allows to obtain almost 100% loading of liposomes with ferrocolloid; however, in the liposomes prepared by this method, no inner aqueous phase is present to accommodate the solution of a pharmaceutical substance. We use another approach: incorporation of the ferrocolloid directly into the lipid phase of the liposomes using the following procedure. First, colloidal gamma-ferric oxide is synthesized by alkaline coprecipitation from the solution of ferric and ferrous salt as described; however, no stabilizer is added during the precipitation step. The ferrocolloid precipitate is extensively washed with distilled water, methanol, and stored in 100% methanol. Necessary amount of ferrocolloid precipitate (0.2°–1.0 mg of iron per 1 mg of total lipids) is washed several times with 100% chloroform; the lipids are dissolved in chloroform and added to the chloroform-washed ferrocolloid precipitate. Phospholipids have strong affinity to the surface of iron oxide particles and transfer them into colloidal state again, now in chloroform. Finally, the chloroform ferrocolloid-lipid solution will be evaporated under the stream of nitrogen and held under vacuum for 2 hours to remove the traces of solvent. At this moment iron oxide will become colloidally dispersed in the lipid film to form what is below called a ferrolipid.

c. Formation of ferroliposomes. In order to optimize the procedure for preparation of ferroliposomes from the ferrolipid we compare the following methods:
  (a) Sonication. Ferrolipid is hydrated with shaking in aqueous buffer (20 mM HEPES, 0.15 M NaCl) or in the solution of a model solute (see below) above Tc. Multilamellar vesicles (MLV) formed in this way are sonicated at the same temperature until clearness (usually 5–6 min). Then the reaction mixture is allowed to cool to room temperature. This method is the simplest and produces small (30–50 nm) unilamellar liposomes.
  (b) Solvent injection and sizing through polycarbonate membrane. Ferrolipid is dissolved in a low-boiling nonpolar solvent (methylene dichloride) and injected into water phase as described [47], the temperature being maintained above Tc. The resulting liposome slurry is put under vacuum to remove residual organic solvent and forced through 0.2 μm Nuclepore polycarbonate filter for sizing and separation of liposomes [48]. This method produces so-called large unilamellar-/oligolamellar vesicles (LUV) and allows higher loads of a solute.
  (c) Rapid extrusion. MLV prepared as above is repeatedly forced through two stacked Nuclepore membranes (0.2 μm) using the syringe extruder similar to the one described in the literature [49]. We have modified the design of the extruder to allow thermostatted operation. Extrusion is be done at a temperature above Tc. Compared to solvent injection, this method allows high loads of the solute without the danger of contamination by an organic solvent [50]; however, it may result in higher losses of iron and/or lipid on the filter. Finally ferroliposomes are passed through Sephadex G-25 desalting column (PD-10, Pharmacia) to remove all low-molecular impurities and stored in refrigerator before use.

Characterization of ferroliposomes.
a. Size and ultrastructure of ferroliposomes are studied by electron microscopy (EM) as described [49]. Briefly, ferroliposomes are applied on the bacitracin-treated carbon-reinforced grids and contrasted with 1% phosphotungstic acid. Size distribution of ferroliposomes is obtained by direct measurements of EM images. Iron oxide is easily recognized at the electron micrographs as dark electron-dense granules ca. 10 nm in diameter, while contours of the lipid phase are negatively contrasted.
b. Iron and lipid concentration. Iron concentration is determined by o-phenantroline method after digestion of an aliquot with conc. $H_2SO_4$ and reduction with ascorbate [51]. Lipid concentration is determined by phosphorous as described [52].

3. Solute release from CF-loaded ferroliposomes and effect of RF-field.

Incorporated solutes are normally released from DPPC/DSPC liposomes at a slow rate. We compare the release of a model substance, 5(6)-carboxyfluorescein (CF) from liposomes as described [45], with some modifications. Liposomes are prepared in the presence of 50 mM CF in 20 mM HEPES and 150 mM NaCl, pH 7.4, and excess CF is removed by two consequent passages through PD-10 desalting column (Pharmacia) equilibrated with 50 mM Na citrate in 20 mM HEPES and 150 mM NaCl buffer (balanced buffer), to balance in ionic strength and osmolarity of outer and inner phases of the liposomes. Samples are stored at RT and in refrigerator, and CF fluorescence of the diluted samples is measured daily to obtain the release curves. It is known that blood serum affects the thermal release of CF from liposomes [42]. In another series of samples we add fetal calf serum to the buffer to compare the effect of serum on the release of liposomes.

Prior to studies of the RF field effect on the CF-loaded ferroliposomes, we ensure that the liposomes do release CF during normal increase of temperature above Tc. Samples of liposomes are incubated in the water bath preheated to temperatures between 25° C. and 55° C. (step 2° C.), quickly cooled in ice and fluorescence of CF measured using Aminco Fluro-colorimeter. A 100% release reading is made in each sample after destruction of liposomes with 0.1% of Triton X-100.

Samples of CF-loaded ferroliposomes diluted with balanced buffer are then placed in the inductor coil of the field generator (described above) and exposed to electromagnetic fields at frequencies in the range of 0.3–1 MHz and field strength 80–150 Gauss. We start with 30–60 sec. exposures and go down according to the observed effect. Bulk temperature of the sample also monitored during exposure. It helps us to understand if the observed effect is due to the local heating of the ferroliposomes or total temperature raise of the sample.

To model the situation in the bloodstream, we pump the suspension of the ferroliposomes through a tubing axially placed inside the inductor coil, at the linear flow rate similar to that of capillary blood flow [53]. Aliquots of the ferroliposomes are taken from the effluent at various times and analyzed for CF fluorescence to obtain a release curve that corresponds to the one expected in vivo. All solute release studies are repeated also in the presence 10% FCS and RPMI/640 cell culture medium.

4. Incorporation of Adriamycin in the thermosensitive ferroliposomes.

Adriamycin (doxorubicin hydrochloride) is of great interest as a targeted anticancer drug because the great therapeutic potential of this anticancer drug is limited by its systemic toxicity, especially cardiotoxicity [54]. Thermosensitive ferroliposomes are loaded with adriamycin using the "remote loading" technique [55]. This technique employs the property of weak lipophilic bases or acids to cross the liposomal membrane in response to transmembrane gradient of pH [56]. Adriamycin, a weak base, spontaneously accumulates in the liposomes with an acidic (pH 4) interior when the exterior buffer is kept at pH 7 or higher. The accumulated drug remains inside liposomes until the transmembrane pH gradient is fully relaxed. Specifically, we prepare ferroliposomes using glutamate buffer at pH 4.6 (interior) and pH 7.5 (exterior) as described for regular DPPC liposomes [55]. The liposomes are incubated with adriamycin at approx. 0.1:1 drug to lipid ratio, aliquots are taken at various incubation times, and liposome-bound adriamycin is determined by its intrinsic fluorescence in the void volume fraction after passage of an aliquot through a small gel-filtration column (NP-10, Pharmacia). If the incubation time required for the loading is too high, which is not unlikely for a phospholipid bilayer below its transition temperature, we perform incubation at temperature above Tc and quench the drug-loaded liposomes by injecting them into the ice-cold buffer. These experiments establish the incubation time and temperature for efficient loading of the thermosensitive ferroliposomes with adriamycin. The unbound drug is removed from the loaded ferroliposomes by gel filtration through Sephadex G-25.

5. Spontaneous and RF-field triggered release of Adriamycin from thermosensitive ferroliposomes.

We compare the release of adriamycin from thermosensitive ferroliposomes in the physiological saline buffer (PBS), PBS +10% fetal calf serum (FCS), and RPMI 1640 cell culture medium +10% FCS under the following conditions:
(a) storage at room temperature and +4° C.;
(b) water bath heating to temperatures above Tc;
(c) exposure to RF electromagnetic field.

The experimental procedures are the same as described above for CF-loaded ferroliposomes, except that the amount of bound adriamycin is determined by fluorometry in the void volume fraction after passage of an aliquot of liposomes through Sephadex G-25 column.

6. Effect of Adriamycin-loaded thermosensitive ferroliposomes on the growth of cancer cells in vitro.

This part of the work explores triggering cell death by exposure of cancer cells to RF electromagnetic field in the presence of Adriamycin-loaded thermosensitive ferroliposomes. We use Adriamycin-sensitive human small cell lung cancer cell lines SHP-77 and H345, routinely maintained in our laboratory. The cells are grown in RPMI 1640 medium plus 10% FCS at 37° C. Ferroliposomes and Adriamycin stock solution are diluted with cell medium and sterilized by filtration. Various doses of sterile ferroliposomes and/or Adriamycin, free or ferroliposome-incorporated, are added to the cells in standard cell-culture 96well plates. To observe the effect of RF field, cell suspension is temporarily transferred to a tissue culture plastic tube inserted into the inductor coil. Growth of the cells is evaluated using our routine ($^3$H)Thymidine incorporation assay [57]. Table 8 describes the experimental design for this study.

The need for site-specific cancer chemotherapy is evident, and the success in this area is still far below this need. This invention includes a totally novel approach to site-specific chemotherapy. The chemotherapeutic substance is incorporated into thermosensitive liposomes together with ferromagnetic microparticles. Such liposomes normally retain their contents for a long time. However, when such liposomes approach the target site exposed to the source of radiofrequency electromagnetic field, the field heats the ferromagnetic particles; they in turn heat the liposome membrane to reach the transition temperature of the lipid and rapidly release the drug into the vascular bed of the target area. The applications of this approach are multifold. Apart from adriamycin, it is possible to use other anticancer pharmaceuticals in the RF field-dependent ferroliposomal targeted delivery as described here. Such important anatomical areas as head, neck, extremities, and skin are very suitable for RF-field application and therefore for the targeted chemotherapy using the described approach; and the recent development of endoscopic RF-field applicators [58] substantially expand this list to include sites close to the walls of body cavities. It indicates that the approach is practical for its final destination, treatment of human patients.

EXAMPLE

EXAMPLE 1

Figure 1:
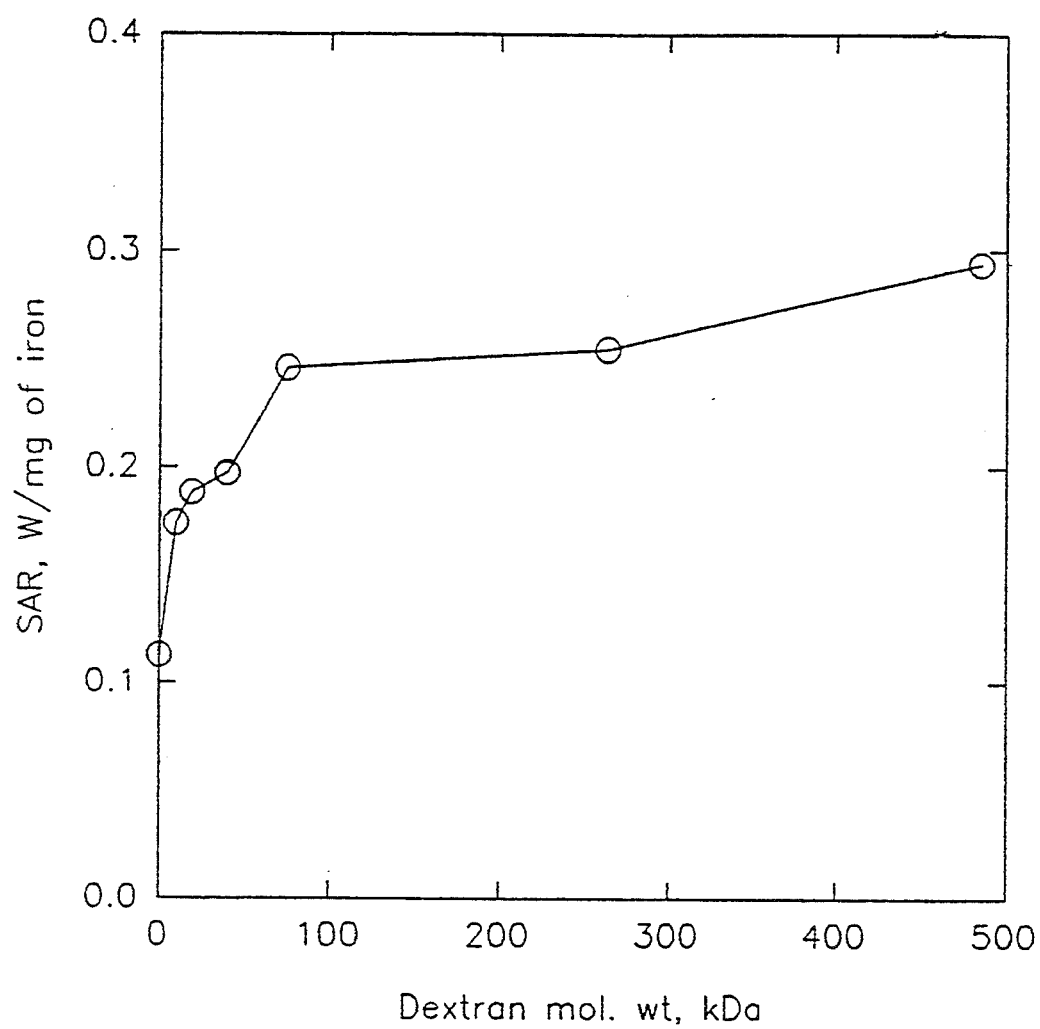
FIG. 1 depicts the dependence between the average molecular mass of dextran and the specific power absorption rate of the ferrocolloids obtained by the inventive procedure (except size fractionation step) and placed in the electromagnetic field with the frequency of 1.1 MHz and field strength 86 Oersted.
Figure 2:
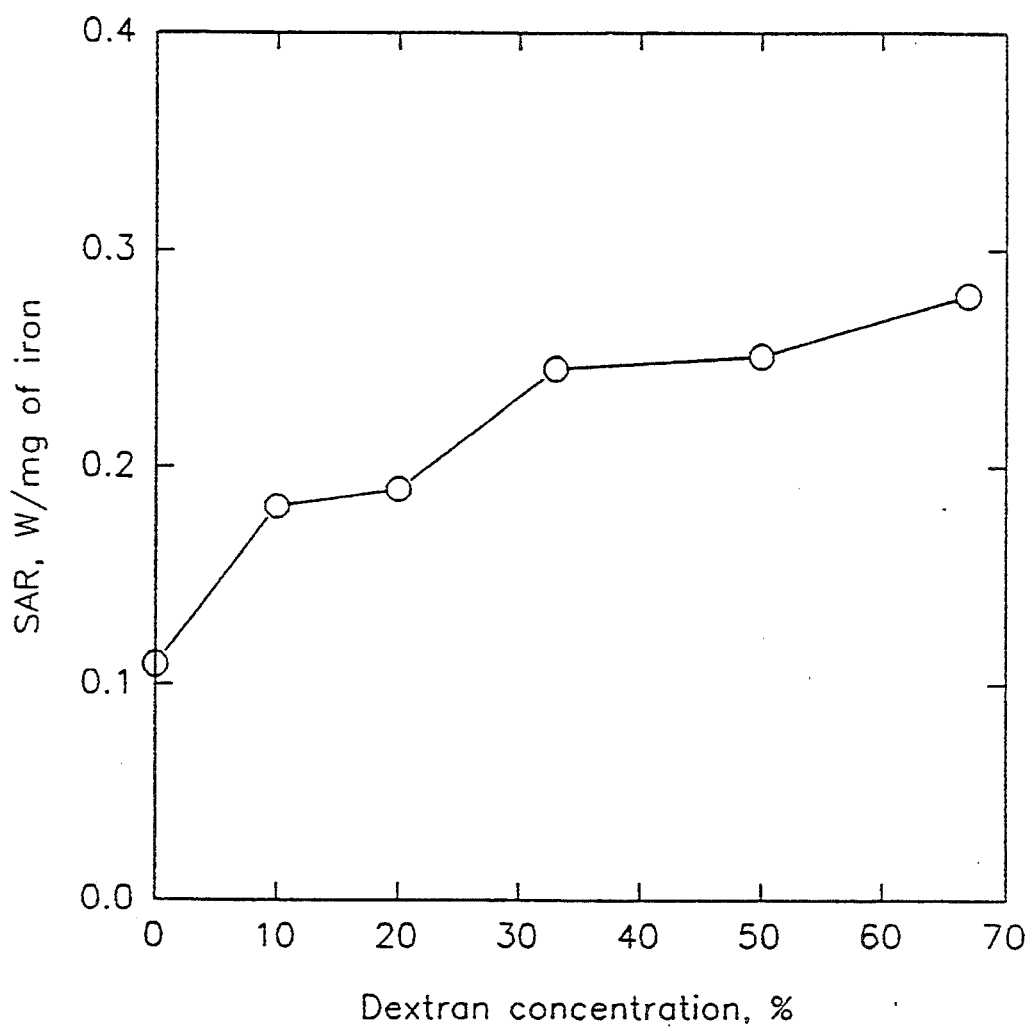
FIG. 2 depicts the dependence between the dextran concentration in the precipitant solution and the specific power absorption rate of the ferrocolloids obtained by the inventive procedure (except size fractionation step) and placed in the electromagnetic field with the frequency of 1.1 MHz and field strength 86 Oersted. Dextran average molecular mass is 74 kilodalton.
Figure 3:
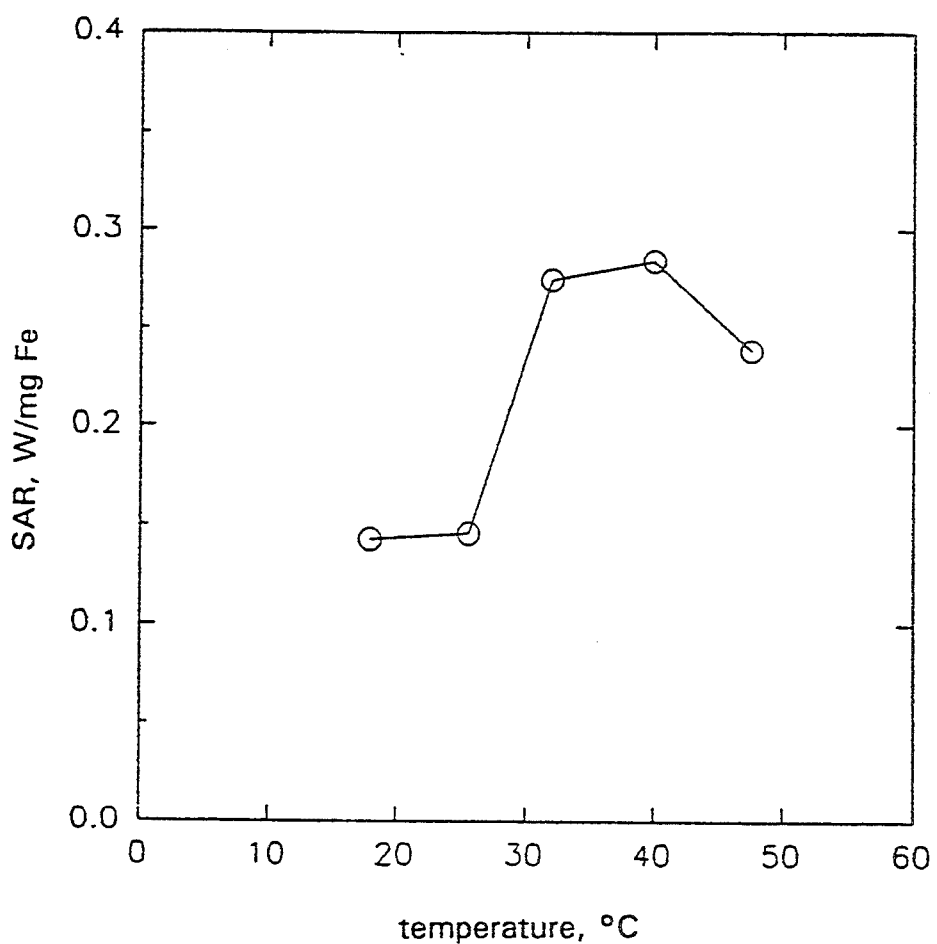
FIG. 3 depicts the dependence between the temperature of the reaction mixture during the iron oxide precipitation step and the specific power absorption rate of the ferrocolloids obtained by the inventive procedure (except size fractionation step) and placed in the electromagnetic field with the frequency of 1.1 MHz and field strength 86 Oersted. Dextran average molecular mass is 76 kilodalton, dextran concentration in the precipitant is 33% (w/w).
Figure 4:
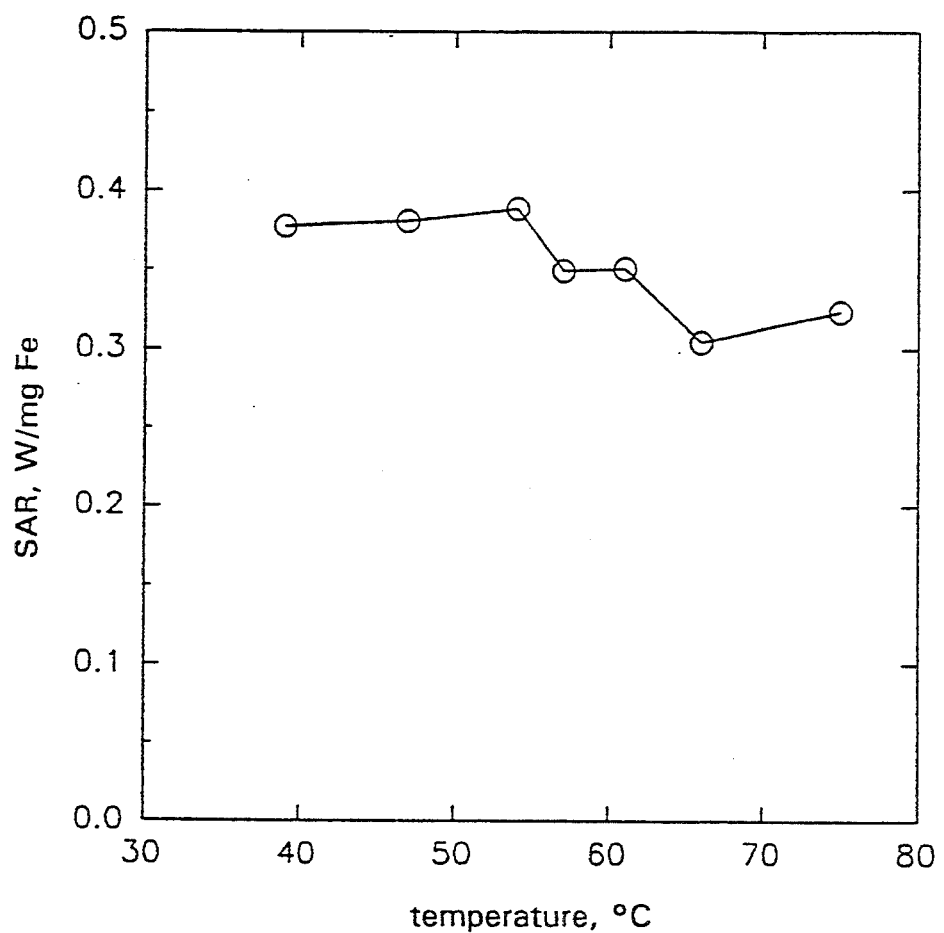
FIG. 4 depicts the dependence between the temperature of the reaction mixture during the heating step after the precipitation of iron oxides and the specific power absorption rate of the ferrocolloids obtained as described for FIG. 3.
Figure 5:
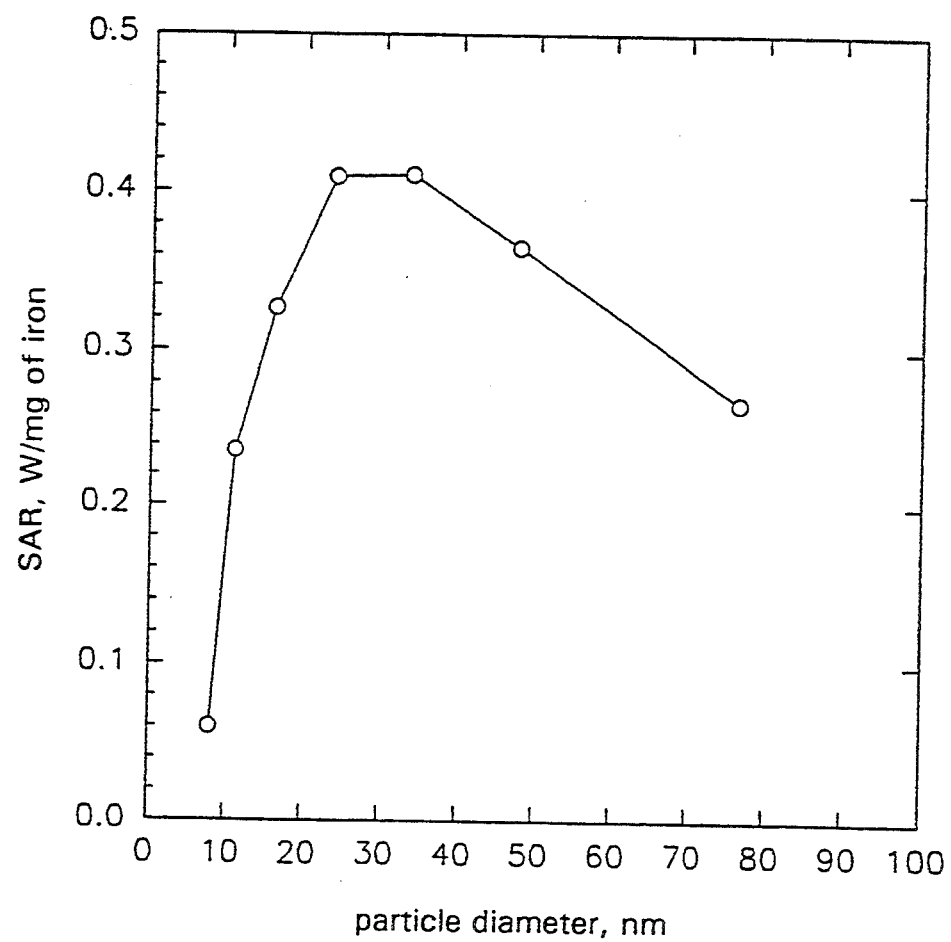
FIG. 5 depicts the dependence between the mean particle size of dextran-coated colloidal magnetic iron oxide obtained by the procedure described in Example 1 and the specific power absorption rate of the particles in the electromagnetic field with the frequency of 1.1 MHz and field strength 86 Oersted. The particles were fractionated by centrifugal pelleting, and the mean particle size was calculated as the geometric mean of the maximum and minimum hydrodynamic diameter of the particles pelleted in each fraction according to the centrifugation data as described in the literature [26].
Figure 6:
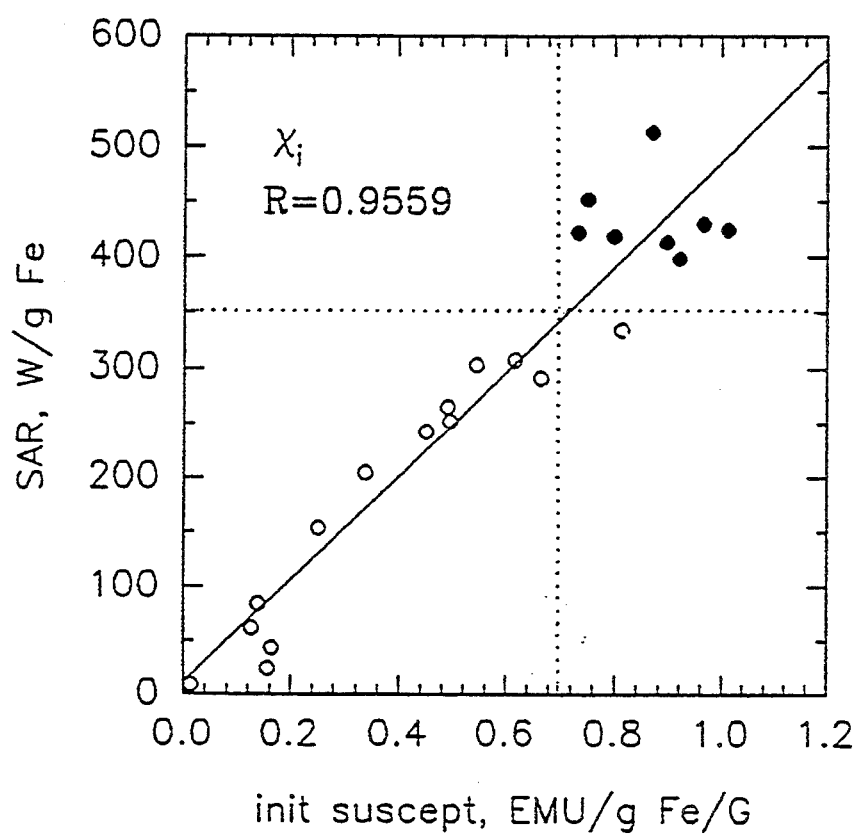
FIG. 6 is a graph of initial magnetic susceptibility vs. SAR for magnetic particles prepared by various methods. Filled dots represent values obtained for ferrocolloids prepared according to the invention. Open dots having SAR values < 100 represent values obtained for ferrocolloids prepared according to methods described in the prior art. Other open dots (SAR > 100) represent values obtained with suboptimal variations of the present invention.
Figure 7:
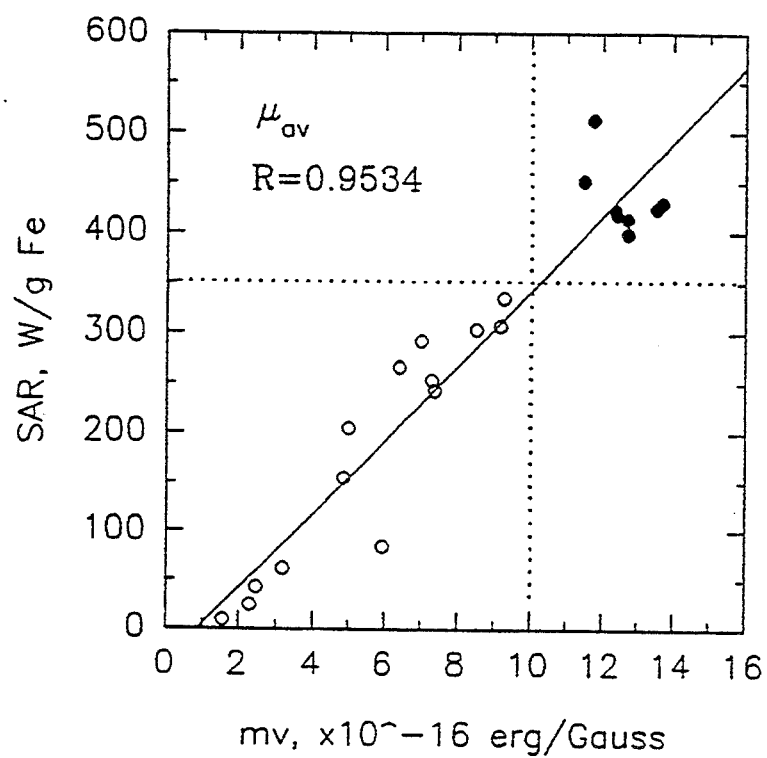
FIG. 7 is a graph of magnetic moment vs. SAR for magnetic particles prepared by various methods. Filled dots represent values obtained for ferrocolloids prepared according to the invention. Open dots having SAR values < 100 represent values obtained for ferrocolloids prepared according to methods described in the prior art. Other open dots (SAR > 100) represent values obtained with suboptimal variations of the present invention.
Figure 8:
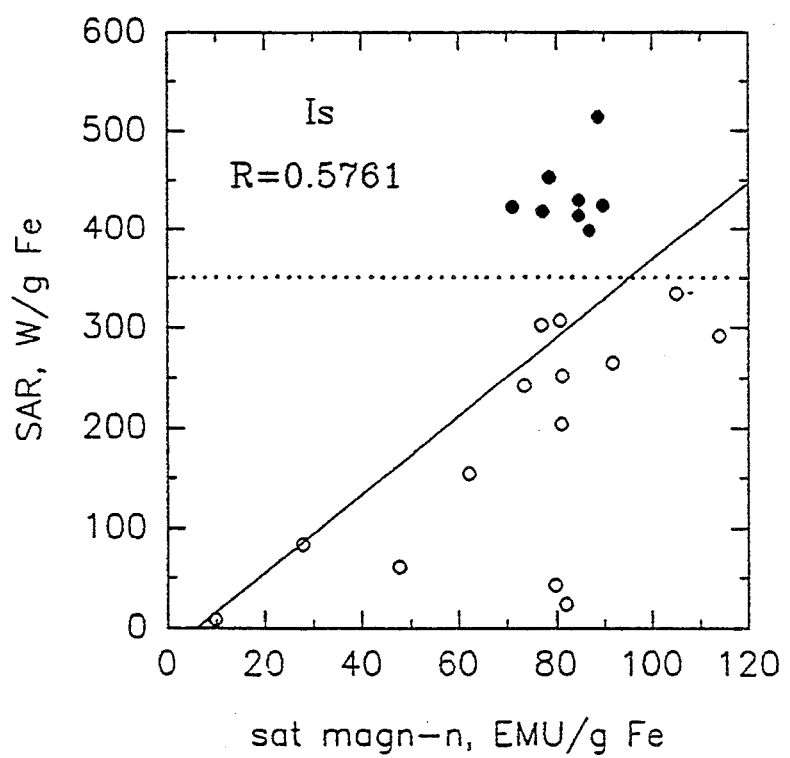
FIG. 8 is a graph of saturation magnetization vs. SAR for magnetic particles prepared by various methods. Filled dots represent values obtained for ferrocolloids prepared according to the invention. Open dots having SAR values < 100 represent values obtained for ferrocolloids prepared according to methods described in the prior art. Other open dots (SAR > 100) represent values obtained with suboptimal variations of the present invention.
Figure 9:
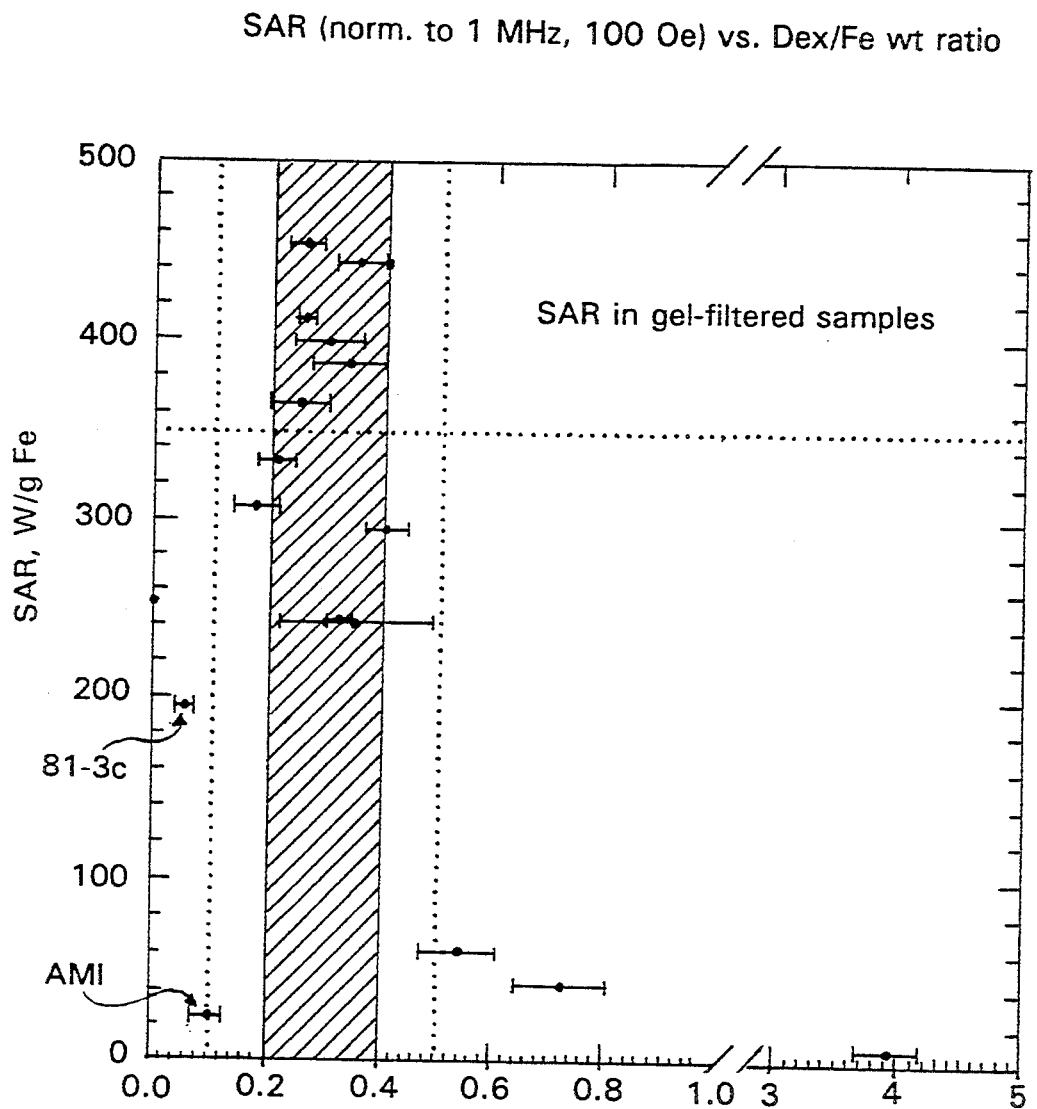
FIG. 9 is a graph of Dextran:Iron ratio (w/w) vs. SAR for magnetic particles prepared according to the invention except for varying the Dextran:Iron ratio. Error bars represent the standard error in determining Dextran:Iron ratio. The value designated 81-3c was a sample prepared according to our procedure described herein, then exposed to citric acid; the value designated AMI was prepared according to the AMI published procedure.
Figure 10:
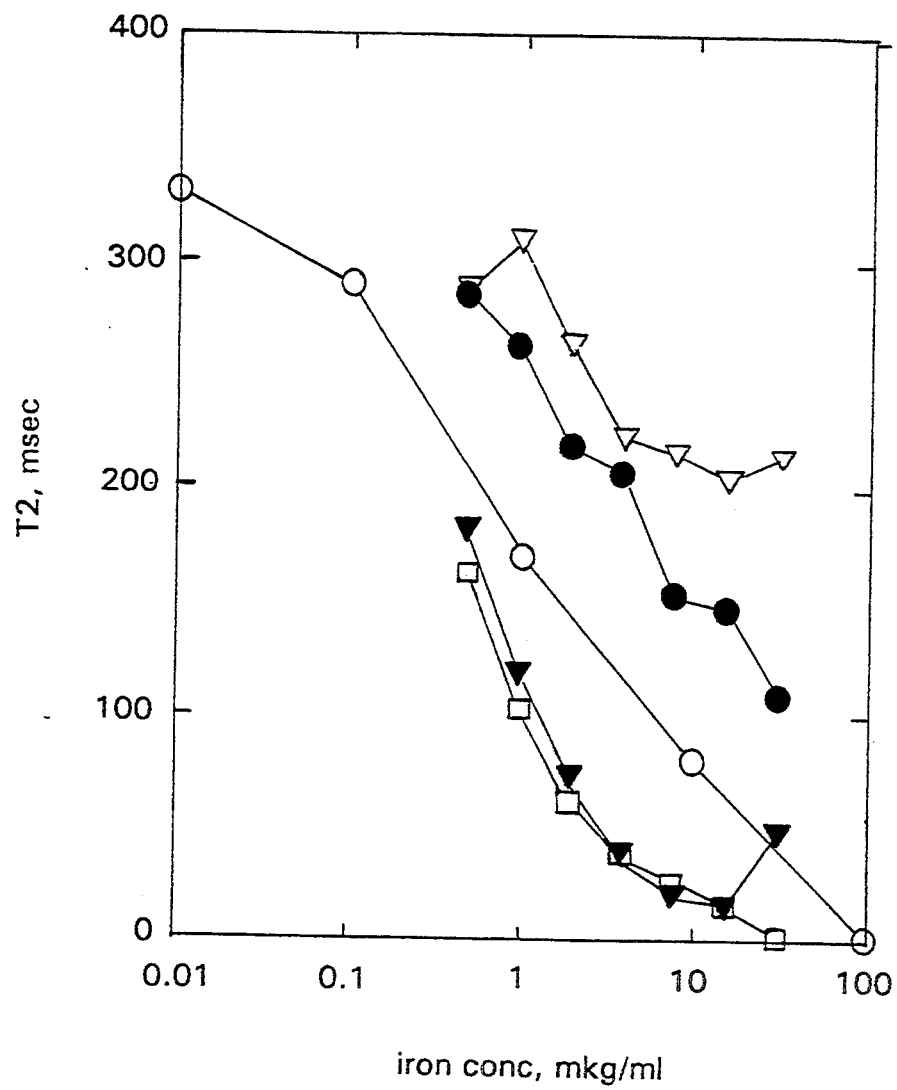
FIG. 10 is a graph of $T_2$ proton relaxation time as a function of iron concentration, comparing magnetic particles prepared according to the invention (filled triangles, open squares), particles prepared without dextran (open triangles), particles prepared with a low dextran content (closed circles), and published values particles prepared according to a prior art protocol (open circles) (Cerdan et al.).
Figure 11:
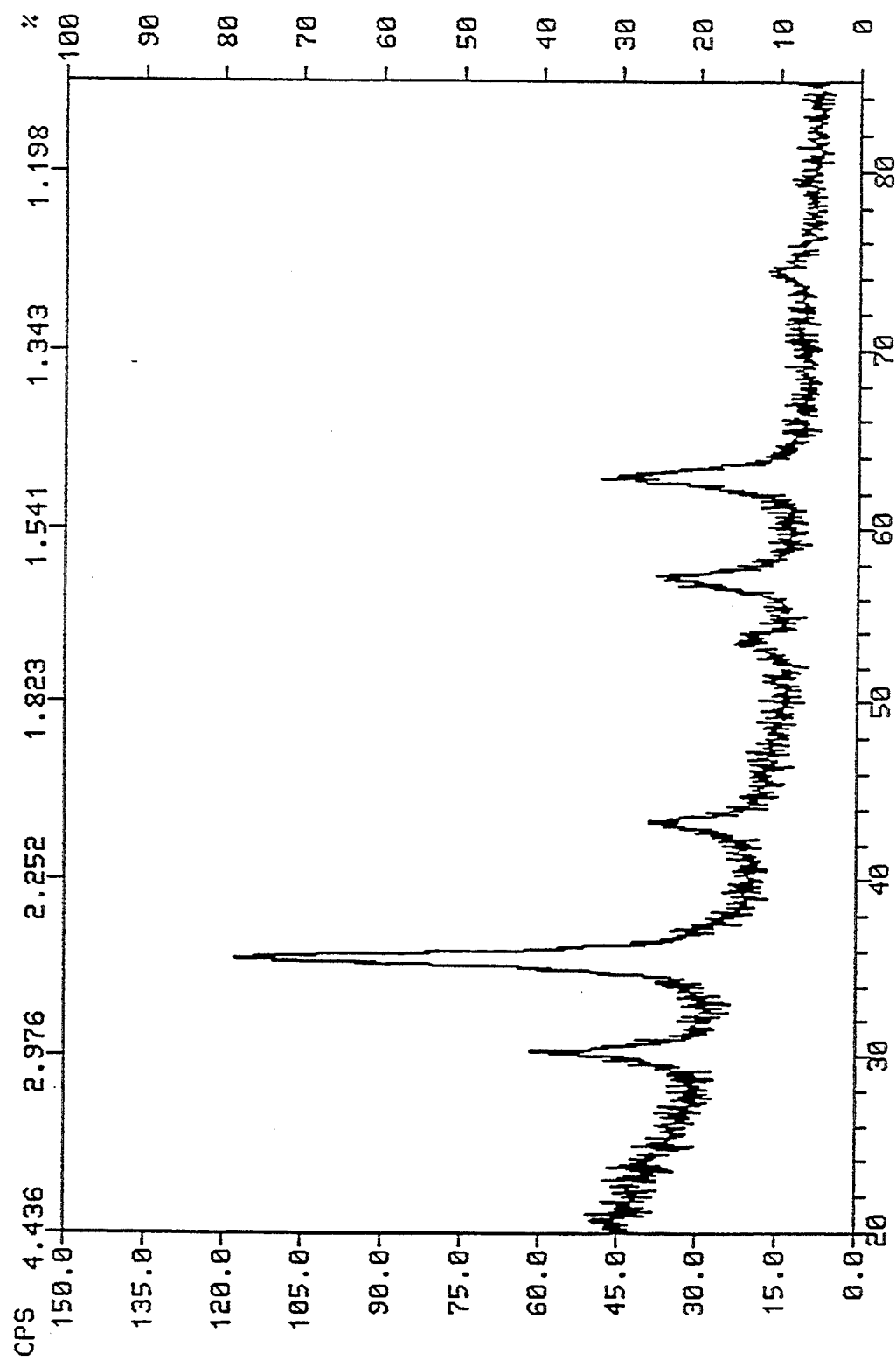
FIG. 11 is a scan of an X-ray diffraction pattern for high-SAR particles prepared according to the invention. The standard powder method of X-ray diffraction was employed. The pattern is consistent with an iron oxide composition essentially entirely $\gamma$-Fe$_2$O$_3$.
Figure 12:
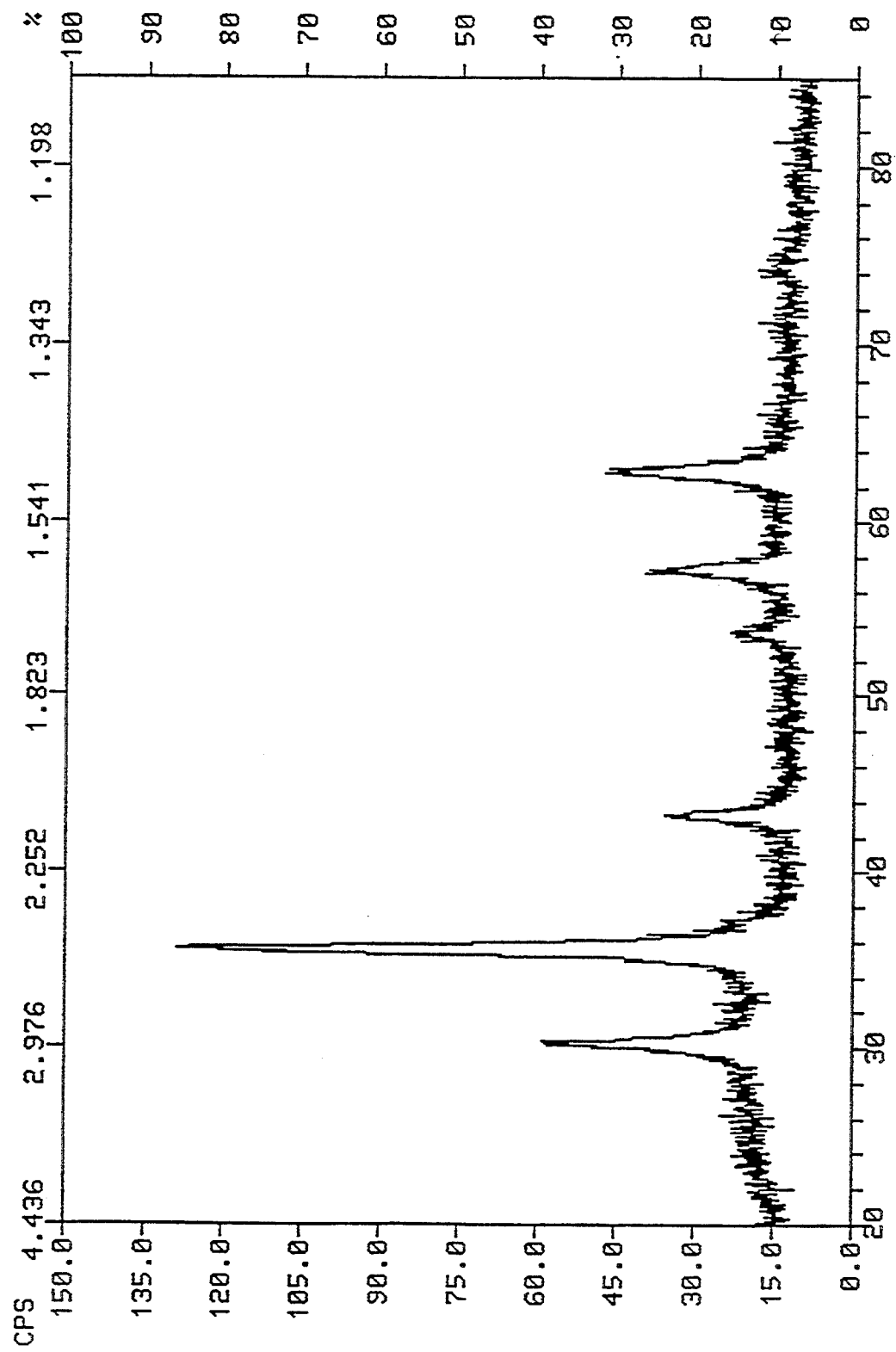
FIG. 12 is a scan of an X-ray diffraction pattern for low-SAR particles produced by a sub-optimal variant of the invention. Conditions were as described for FIG. 11.
Figure 13:
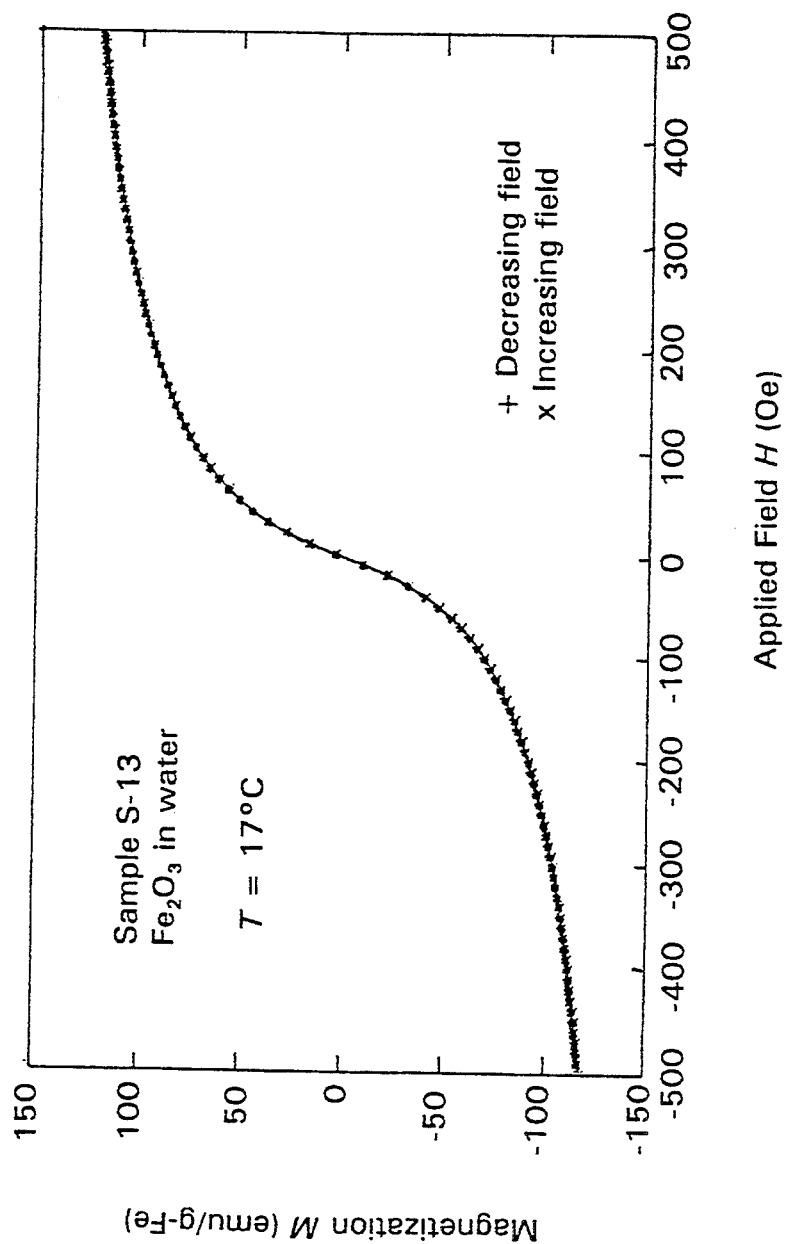
FIG. 13 is a magnetization curve of particles prepared according to the invention. The paths of magnetization and demagnetization are virtually superimposed, indicting that the particles are essentially completely superparamagnetic with little, if any, ferromagnetism.

Synthesis of the dextran-coated magnetic iron oxide colloids.

6 g of $FeCl_3 6H_2O$ and 3 gm of $FeCl_2 4H_2O$ are dissolved in 26 ml deionized water. 3 ml of this solution is transferred into a thermostatted container with a tapered sonication probe ($\frac{1}{8}$ in. Branson Ultrasonic) immersed into the liquid. 4 g of Dextran (Mol. wt 76,000) is dissolved in 12 ml of concentrated (28.4 wt%) aqueous ammonia. The probe is attached to a Model W185 Sonifier (Heat Systems-Ultrasonics), and the solution is thermostatted at 30° C. Sonication starts at the lowest power setting, and the dextran-ammonia solution (2 ml) is added dropwise to the iron solution with thorough mixing. Then 1 ml of concentrated ammonia and 2 ml of deionized water are added to the reaction mixture, sonication stopped, and the temperature of the reaction mixture is increased to 50° C. After 15 min. incubation, the mixture is neutralized with concentrated acetic acid, stirred thoroughly, and centrifuged to remove gross aggregates. The supernatant fluid is dialyzed extensively against water and filtered through 0.2 μm microfilter to give 11 ml of a dark brown sol with iron concentration 10.9 mg/ml. Yield of ferrocolloid 59% (iron), SAR 364 W/g of Fe (1 MHz, 100 Oersted). After separation of unbound dextran by gel-filtration (Sephacryl S-400): iron 61.5% (wt), dextran 38.5% (wt).

EXAMPLE 2.

Size fractionation of the ferrocolloid.

Dry sucrose is added to the sol of dextran-coated magnetic iron oxide obtained according to the Example 1, to 5% final concentration. The sol is centrifuged using high speed centrifuge (Beckman J2-21M equipped with JS-13.1 rotor) at 25° C. to collect the fraction of particles having sedimentation constants in the range of 900–1800 S ($D_{eff}$ 20.1–28.5 nm). Yield 62.1% of the iron taken for fractionation; SAR 515 W/g of Fe (1 MHz, 100 Oe). Magnetization curve (water, 18° C.): static initial susceptibility of the particle bulk $X_i$=3.04 EMU/cm$^3$/Gauss, saturation magnetization $I_s$=305 EMU/cm$^3$.

EXAMPLE 3

Synthesis of a ferrocolloid with purification by high gradient magnetic separation.

Precipitation of iron oxides and heat treatment are performed as in Example 1. After low speed centrifugation, the supernatant is extensively dialyzed against distilled water, and pH of dialyzate is adjusted to 9.5–10.0. The dialyzate is centrifuged at 15,600 g 30 min., and the supernatant recovered. 0.5 g of commercial steel wool (finest grade) is washed with ethanol followed by distilled water and packed into a column 1 cm in diameter. The column is placed into a gap of Neodymiun-Iron-Boron horseshoe magnet, and the supernatant is applied onto the column. After the passage of the sample, the column is washed with equal volume of distilled water, stoppered, and the magnet removed. The ferrocolloid is eluted with distilled water and further concentrated by precipitation with equal volume of 95% ethanol. SAR 474 W/g Fe (1 MHz, 100 Oersted), saturation magnetization $I_s$=360 EMU/cm$^3$.

TABLE 1

Comparison of different ferromagnetic materials for hyperthermia

| Material | SAR, W/gm of material (a) | Ref. on the use in hyperthermia | Remarks/Source of data or materials |
|---|---|---|---|
| Oxidized carbonyl iron ($Fe_2O_3$) | Non-detectable | [3–5] | Heating at 1.2 MHz starts at 140 Oe |
| Ceramic-magnetic iron composite | 5.67 | [10,11] | 1 gm of material per gm of tumor was used for tumor heating [ ]. |
| Metal iron powder (reduced iron) | 17.5 | [6,7] | Determined by the authors |
| Barium hexaferrite powder | 1.93 | [12] | Determined by the authors |
| Aqueous dispersion of magnetite | 32.5 (46.4 W/gm Fe) | [8–10] | Ferrofluidics Corp. (Nashua, NH, USA) Ferrofluid EMG-1111 |
| Magnetite stabilized with ammonium laurate micelles | 189 (266 W/gm Fe) | Not reported | Prepared according to [17]; not suitable for use in living organisms |
| Dextran-magnetite NaOH-precipitated | Non-detectable | Not reported | Prepared according to [18] |
| Modified (oxidized-alkali treated) dextran-coated magnetite | 6.21 (8.75 W/gm Fe) | [15,16] | Prepared according to [16]; reported concentration for tumor heating in mice 12 mg Fe/gm tissue |
| Dextran-magnetite, precipitated by ammonia (prototype preparation) | 31.8 (45.5 W/gm Fe) | Not reported | Prepared according to [25] |
| Dextran-coated magnetic iron oxides, prepared according to the present invention: | | [29–32] | |
| S-13 | 280 (400 W/gm Fe) | | No size fractionation |
| SDK-19-2 | 320 (455 W/gm Fe) | | No size fractionation |
| S67-P3 | 360 (515 W/gm Fe) | | Size-fractionation used |

(a) Normalized to frequency f = 1 MHz, field amplitude H = 100 Oersted using the formula: SAR = k · f · H$^2$.

TABLE 2

Effect of ultrasonic energy treatment and of the mode of mixing of the reagents on the heating properties of ammonia-precipitated dextran-coated colloidal magnetic iron oxides. Ultrasound applied throughout the iron oxide precipitation and heat treatment steps.

| Mode of Mixing | Ultrasonic Treatment | SAR, W/G of Fe[a] |
|---|---|---|
| Ammonia added dropwise to iron(II) and iron(III) chloride solution, no dextran | No | 167 |
| Ammonia added dropwise to iron(II) and iron(III) chloride solution, no dextran | Yes | 144 |
| Dextran (M.m. 74 kD) dissolved in the iron(II) and iron(III) chloride solution, ammonia added dropwise | No | 206 |
| Dextran (M.m. 74 kD) dissolved in the iron(II) and iron(III) chloride solution, ammonia added dropwise | Yes | 336 |
| Dextran dissolved in ammonia; dextran-ammonia solution added dropwise to the solution of iron(II) and iron(III) chlorides | No | 256 |
| Dextran dissolved in ammonia; dextran-ammonia solution added dropwise to the solution of iron(II) and iron(III) chlorides | Yes | 400 |

TABLE 3

Effect of ultrasonic treatment applied at various steps of the synthesis. Aqueous solution of iron(II) and iron(III) chloride was precipitated by dropwise addition of dextran (M.m. 76 kilodalton) solution in concentrated aqueous ammonia and heated at 70° C. for 10 min.

| Period of ultrasonic treatment | Relative SAR[a] |
|---|---|
| Throughout precipitation and heat treatment steps | 100% |
| During precipitation: | |
| until neutralization point | 52.4% |
| from neutralization point to the end of precipitation (pH 9.85) | 95.8% |
| during the whole precipitation step | 121.4% |
| During heat treatment step only | 22.3% |
| No ultrasound applied | 30.4% |

[a])At the frequency 1 MHz, field amplitude 100 Oersted.

TABLE 4

Amounts of ferromagnetic materials required to raise and maintain tumor (treatment volume) temperature at +43° C. Calculations were made according to [33] and [34]. Treatment volume perfusion assumed to be equal to that of the surrounding tissue, tissue density 1 g/cm³, and body temperature +37° C. EM field parameters, $f = 1$ kHz, $H = 100$ Oersted.

| Tumor size, cm | Required power deposition W/cm³ of tumor | Amount of ferromagnetic material, mg of iron per 1 gram of tumor | | | |
|---|---|---|---|---|---|
| | | According to the Examples 1 and 2 of the present invention | U.S. Pat. No. 4,574,782 [11] | WO90/01,939 [16] (mg of material) | U.S. Pat. No. 5,057,952 [7] |
| Case A. Tumor in the area with average perfusion $W_n = 1.67$ kg/m³/s (muscle). | | | | | |
| 1 | 0.608 | 1.18 | 107 | 69.5 | 34.7 |
| 3 | 0.149 | 0.289 | 26.3 | 17.0 | 8.51 |
| 5 | 0.096 | 0.186 | 16.9 | 11.0 | 5.49 |
| 10 | 0.0645 | 0.125 | 11.4 | 7.37 | 3.69 |
| Case B. Tumor in the area with high perfusion $W_n = 10$ kg/m³/s (brain) | | | | | |
| 1 | 1.11 | 2.16 | 196 | 127 | 63.4 |
| 3 | 0.450 | 0.873 | 79.4 | 51.4 | 25.7 |
| 5 | 0.354 | 0.687 | 62.4 | 40.5 | 20.2 |
| 10 | 0.295 | 0.527 | 52.0 | 33.7 | 16.9 |

TABLE 5

In vivo heating of tumors using ferrocolloids prepared according to the invention. Field amplitude proportional to coil voltage (approx. 75 Oersted at 2.2 kV).

| Experiment # | Tumor Type | Tumor mass, g | Injected iron, mg | Tumor concentration of the ferrocolloid, mg Fe/gm tissue | Tumor temperature differential, initial minus stationary, °C. | Temperature differential, tumor minus rectal, °C. | Stationary tumor temperature achieved in time, min | Coil voltage, kV |
|---|---|---|---|---|---|---|---|---|
| 1 | A549 | 2.54 | 2.10 | 0.83 | 12.4 | 4.8 | 18 | 2.2 |
| 2 | A549 | 0.93 | 0.90 | 0.97 | 7.8 | 4.8 | 12.5 | 2.4 |
| 3 | A549 | 1.37 | 0.61 | 0.45 | 8.2 | 1.6 | 20 | 2.4 |
| 4 | A549 | 5.22 | 3.05 | 0.58 | 13.2 | 8.2 | 23 | 2.2 |
| 5 | SHP77 | 2.88 | 1.83 | 0.64 | 10.0 | 5.2 | 29 | 2.2 |
| 6 | A549 | 3.90 | 2.04 | 0.52 | 11.8 | 7.0 | 7 | 2.3 |

TABLE 6

| Sample | SAR as prepared | SAR, W/g Fe (1 MHz, 100 Oe) exposed to 50 mM sodium citrate pH 6.0, for 24 hours | % Change |
|---|---|---|---|
| s81-2s | 375.0 | 197.2 | −47.4% |
| s81-3s | 400.5 | 230.5 | −42.5% |
| s81-4s | 359.1 | 212.1 | −40.9% |

TABLE 7

| Sample | Dextran lot and M.w. (Sigma Chemical Co.) | Yield of particles % to iron taken | SAR, W/g Fe (1 MHz, 100 Oe) |
|---|---|---|---|
| s82-1s | 13HO123 70,400 | 45.7 | 417.2 |
| s82-2s | 119F0078 71,200 | 45.3 | 404.9 |
| s82-3s | 58H0457 72,600 | 47.6 | 395.3 |
| s82-4s | 120H0176 74,200 | 50.4 | 418.0 |
| s82-5s | 22H0606 76,000 | 43.3 | 382.1 |
| s82-6s | 75C0170 264,000 | 41.5 | 424.2 |

TABLE 7-continued

| Sample | Dextran lot and M.w. (Sigma Chemical Co.) | Yield of particles % to iron taken | SAR, W/g Fe (1 MHz, 100 Oe) |
|---|---|---|---|
| Average ± SD | | 45.6 ± 3.14 | 407 ± 160 |
| Standard deviation (SD)., % | | 6.88% | 3.94% |

TABLE 8

| Group # | Sample | RF Field | Dose dependence |
|---|---|---|---|
| 1 | PBS | No | N/A |
| 2 | PBS | Yes | N/A |
| 3 | Adriamycin, solution | No | Yes |
| 4 | Adriamycin, solution | Yes | Yes |
| 5 | Ferroliposomes, unloaded | No | Yes[1] |
| 6 | Ferroliposomes, unloaded | Yes | yes |
| 7 | Ferroliposomes, unloaded + Adriamycin, solution | No | Yes[2] |
| 8 | Ferroliposomes, unloaded + Adriamycin, solution | Yes[3] | Yes[3] |
| 9 | Adriamycin in ferroliposomes | Yes | Yes |
| 10 | Adriamycin in ferroliposomes | No | Yes |

NOTES:
[1])Dose of ferroliposomes (iron) is varied.
[2])($^3$H)Thymidine incorporation vs. Adriamycin concentration is done for highest expected dose of ferroliposomes.
[3])Done if any effect of the field is observed in the groups #4 and #6.
The differences between ($^3$H)Thymidine incorporation vs. drug dose curves for the above groups are evaluated using conventional statistical tests.

TABLE 9

| Polymers Tested | SAR, w/gm Fe at 1 MHz 100 Oersted |
|---|---|
| Dextrans, M.wt 70,000-76,000 | 440-490 |
| Polyvinylpyrrolidone, M.wt. 40,000 | 194 |
| Ficoll, M.wt 400,000 | 494 |
| DEAE-Dextran, M.wt 2,000,000 | 384 |
| Dextrin, from corn (Sigma Type I) | 177 |
| Ficoll, M.wt 70,000 | 341 (before size selection) |
| | 419 (after size selection) |
| Inulin, from chicory roots | 45.6 |
| Arabic acid (purified gum arabic polysaccharide) | 202 |
| Gum arabic | 149 |
| Chondroitin sulfate A (cartilage polysaccharide) | 263 (before size selection) |
| | 298 (after size selection) |
| Xylan from oat spells (Sigma X-0627) | 274 (before size selection) |
| | 344 (after size selection) |
| Gum tragacanth (polysaccharide) | 124 |
| Dextran-coated iron oxide supplied by Shering AG (Germany) - personal communication | 223 |

REFERENCES

1. Oleson J. R., Calderwood S. K., Coughlin C. T., et al. "Biological and clinical aspects of hyperthermia in cancer therapy", Am.J.Clin. Oncol., 11(3):368-380, 1988.
2. Perez C. A., Emami B., Myerson R. J., et al. "Hyperthermia"—In: Principles and practice of radiation oncology, Lippincott, Philadelphia, 396-446, 1992.
3. Gilchrist R. K., Medal R., Shorey W. D., et al., "Selective inductive heating of lymph nodes", Ann Surg, 140:596-606, 1957.
4. Medal R., Shorey W., Gilchrist R. K., et al. "Controlled radio-frequency generator for production of localized heat in intact animal", Arch Surg 79:427-431, 1959.
5. Gilchirst R. K., Shorey W. D., Hanselman R. C., et al. "Effect of electromagnetic heating on internal viscera: a preliminary to the treatment of human tumors" Ann Surg, 161:890-896, 1982.
6. Hase M., Sako M., Fujii M., et al. "Experimental study of embolo-hyperthermia for treatment of liver tumor—induction heating to ferromagnetic particles injected into tumor tissue", Nippon Igaku Hoshasen Gakkai Zasshi, 49(9):1171-1173, 1989.
7. "A method and apparatus for treating malignant tumors by local hyperpyrexia", U.S. Pat. No. 5,067,952 (1992)
8. Barybin A. S., Medvedeva L. A., Rukhman A. A., "Local hyperthermia with the use of ferromagnetic fluids", In: Radiomodifiers in the radiation therapy of tumors (Radiomodificatory v luchevoi terapii opukholei)—Obninsk, USSR, 48-49, 1982.
9. Gordon R. T., Hines J. R., Gordon D., "Intracellular hyperthermia: a biophysical approach to cancer treatment via intracellular temperature and biophysical alterations", Med. Hypotheses, 5: 83-102, 1979.
10. Borrelli N. F., Luderer A. A., Panzarion J. N. "Hysperesis heating for the treatment of tumors", Phys. Med. Biol. 29(5):487-494, 1984.
11. "Radio frequency-induced hyperthermia for tumor therapy", U.S. Pat. No. 4,574,782 (1986)
12. Jones S. K., Gray B. N., Burton M. A., et al. "Evaluation of ferromagnetic materials for low-frequency hysteresis heating of tumors", Phys Med Biol 37(1):293-299, 1992.
13. Syrkin A. B., Brusentsov N. A., "Ferri- and ferromagnetics in experimental oncology and medicine", Abstr. 6th Int. Conf. Magnetic Fluids, Paris, 480-481, 1992.
14. Autenshlyus A. I., Brusentsov N. A., "Magnetic-sensitive dextran-ferrite immunosorbents" Abstr 6th Int Conf Magnetic Fluids, Paris, 486-487, 1992.
15. Tazawa K., Takemori S., Nagae H., et al. "A study of inductive heating for cancer with use of dextran magnetite (DM): characteristics of dextran magnetite", In: Hyperthermic Oncology. Proc. 6th Int. Congress, Tucson, Ariz., vol. 1, 153, 1992.
16. "Dextran-metal complexes for thermal treatment of cancer", PCT Int Appl WO90/01,939 (1990), JP Apl. 88/204,814, (1988).
17. Pouliquen D., LeJeune J. J., Perdrisot R., et al., "Iron oxide nanoparticles for use as an MRI contrast agent: pharmacokinetics and metabolism", Magnetic Resonance Imaging, 9: 275-283, 1991.
18. Owen C. S., "Magnetic cell-sorting using colloidal proteinmagnetite", J Immunogenetics, 16: 117-123, 1989.
19. Bieva C. J., Vander Brugghen F. J., Stryckmans P., "Malignant leukemic cell separation by iron colloid immunomagnetic adsorption", Exp Hematol, 178: 914-920, 1989.
20. Bacon B. A., Stark D. D., Park C. H., et al., "Ferrite particles: a new magnetic resonance imaging contrast agent. Lack of acute or chronic hepatotoxicity after intravenous administration", J. Lab. Clin. Med., 110(2):164-171, 1987.
21. Weissleder R., Stark D. D., Engelstad B. L., et al., "Superparamegnetic iron oxide: pharmacokinetics and toxicity", Am J Radiology, 152: 167-173, 1989.
22. Molday R. S., Mackenzie D., "Immunospecific ferromagnetic iron-dextran reagents for the labeling and magnetic separation of cells", J. Immunol Methods, 52: 353-367, 1982.
23. "Magnetic iron-dextran microspheres", U.S. Pat. No. 4,452,773 (1984).
24. Ocheltree K. B., Frizzell L. A., "Determination of power deposition patterns for localized hyperther- 24. ...mia: a transient analysis", Int J. Hyperthermia, 4(3):281–305, 1988.
25. Roemer R. B., "Optimal power deposition in hyperthermia. 1. The treatment goal: the ideal temperature distribution: the role of large blood vessels", Int J. Hyperthermia, 7 (2): 317–341, 1991.
26. Nichols J. B., Kraemer E. O., Bailey E. D., "The particle size and constitution of colloidal ferric oxide", J. Phys. Chem., 26: 326–339, 1932.27.
27. Gupta P. K., Hung C. T., Life Sci., 44:175–186, 1989.
28. Papissov M., et al., Antibiotics and Chemotherapy (Moscow), 33:744–757, 1988.
29. Drug Targeting Proc. Symp., Nyon, Switz., 1984.
30. Gregoriadis G., et al., In: Biology of the Cell, 47:11–18, 1983.
31. Allen T., Chohn A., FEBS Lett., 223:42–46, 1987.
32. Gabizon A., Papahadjopoulos D., Proc. Natl. Acad. Sci. 85:6949–6953, 1988.
33. Juliano R., "Optimization of Drug Delivery" Alfred Benzon Symp. 17, Copenhagen, 405–415, 1982.
34. Wolfson S. D., Kirpotin D. B., J. Microbiol. Epidemiol. Immunobiol. (Moscow), 11:73–76, 1987.
35. DeCuyper M., Joniau M., Eur. Biophys. J., 15:311–319, 1988.
36. DeCuyper M., Joniau M., Biochim. Biophys. Acta, 1027:172–178, 1990.
37. Szoka F., Papahadjopoulos D., Ann. Rev. Biochem. Biophys., 9:467–508, 1980.
38. Leserman L., Machy P., in Liposomes. From Biophysics to Therapeutics, M. Ostro, ed. Marcell Dekker, New York, 157–194, 1987.
39. Gregoriadis G., Neerunjun D. E., Biochem. Biophys. Res. Commun., 65:452–, 1976.
40. Rosenberg O. M., Bekreneva V. Y., Loshakova L. V., et al., Bull. Exp. Biol. Med. (Moscow), 97:670–672, 1984.
41. Drug and Enzyme Targeting, Pt.1 ., Widder K. J., Green R., eds. Meth. Enzymol., Vol. 112, AP, New York, 1985.
42. Yatvin M. B., Weinstein J. N., Dennis W. H., et al., Science, 202:1290–1293, 1978.
43. Weinstein J. N., Magin R. L., Yatvin M. B., et al., Science 204:188–191, 1979.
44. Sullivan S. M., Huang L., Biochim. Biophys. Acta 812:116–126, 1985.
45. Weinstein J. N., Ralston E., Leserman L. D., et al., in: Liposome Technology, Vol. 3, Ch. 13, G. Gregoriadis, ed., CRC Press, Boca Raton, 1984.
46. Margolis L. B., Namiot V. A., Kliukin L. M., Biochim. Biophys. Acta 735:193–195, 1983.
47. Deamer D. W., in: Liposome Technology, Vol. 1, Gregoriadis G., ed.,CRC Press, Boca Raton, Fla., 29–35, 1984.
48. Olson F., Hunt C. A., Szoka F. C., et al., Biochim. Biophys. Acta, 557:9–23, 1979.
49. MacDonald R. C., MacDonald R. I., Menco B. P. M., et al., Biochim. Biophys. Acta, 1061:297–303, 1991.
50. Mayer L. D., Hope M. J., Cullis P. R., Biochim. Biophys. Acta, 858:161–168, 1986.
51. Willard H. H., Merritt L. L., Dean J. A., in: Instrumental Methods of Analysis, Van Nostrand, New York, 113–120, 1974.
52. "Biological membranes. A practical approach", Findlay J. B. C., Evans W. K., eds. Oxford, IRL Press, 1987.
53. Song C. W., Cancer Res. (Suppl) 44:4721s–4730s, 1984.
54. Allen A. A., in: The Chemotherapy Source Book, Perry M. C., ed. Williams and Wilkins, Baltimore, Ch. 34, 1992.
55. Mayer L. D., Bally M. B., Cullis P. R., Biochim. Biophys. Acta, 857:123–126, 1986.
56. Nichols J. W., Deamer D. W., Biochim. Biophys. Acta, 455:269–271, 1976.
57. Bunn P. A., Chan D., Dienhart D. G., et al., Cancer Res. 52:24–31, 1992.
58. Yerushalmi A., Fishelovitz Y., Singer D., et al., J. Oncol. 133:873–876, 1985.
59. Overgaard J. (ed), "Hyperthermic Oncology, 1985", vol. 1, 2. Taylor and Francis, London, 1985.
60. Sugahara T., Saito M. (eds.), "Hyperthermic Oncology, 1988", vol. 1, 2. Taylor and Francis, London 1988.
61. Sapozink M. D., Cetas T., Corry M., et al., Int. J. Hyperthermia, 4:1–15, 1988.
62. Perez C. A., Emami B., Nussbaum G., Sapareto S., in: Perez C. A. and Brady L. (eds), "Priciples and Practice of Radiation Oncology", 317–352 1987.
63. International Consensus Meeting on Hyperthermia, Final Report, Intern. J. Hyperthermia, 6:837–887, 1990.
64. Widder K. J., Senyei A. E., Scarpelli D. G., Proc. Soc. Expt. Biol. Med., 58:141–146, 1978.
65. Ranney D. F., Huffaker H. H., Ann. N.Y. Acad. Sci., 507:104–119, 1987.
66. Allan T. M., Hansen C., Martin F., et al., Biochim. Biophys. Acta 1066:29–36, 1991.
67. Allen T. M., Hansen C., Biochim. Biophys. Acta 1068:133–141, 1991.
68. DeCuyper M., Joniau M., Biochim. Biophys. Acta 1027:172–178 1990.
69. Reimers G. W., Khallafala S. E., Br. Patent #1439031, 1976.
70. Maruyama K., Kennel S. J., Huang L., Proc. Natl Acad. Sci. USA 87:5744–5748, 1990.
71. Longley C., Furmanski P., Dienhart D. G., et al., Cancer Res., 50:5954–5961, 1990.
72. Dienhart D. G., Schmelter R. F., Lear J. L., et al., Cancer Res., 50:7068–7076, 1990.
73. Rand R. W., U.S. Pat. No.4,983,159, 1991.
74. Hill D. A., Bioelectromagnetics, 5:131–146, 1984.
75. Dische Z., Methods of Biochemical Analysis, Glick D. (ed), 2:313–358, Wiley, N.Y., 1955.
76. Dewey W. C., Hopwood L. E., Sapareto S. A., et al, Radiology, 123:463–474, 1977.
77. Higgins J. A. , Biological Membranes. A Practical Approach. Findlay J. B. C., Evans W. K. (eds), 113–128, Oxford, IRL Press, 1987.
78. Leserman L., Machy P., Liposomes. From Biophysics to Therapeutics, Ostro M. (ed), 157–194, Marcell Dekker, New York, 1987.
79. Hill D. A., Bioelectromagentics, 6:33–40, 1985.
80. Bacon B. R., Tavill A. S., Brittenham G. M., et al., J. Clin. Invest. 71:429–39, 1985.

We claim:

1. A composition comprising particles of an iron oxide and a polymer, said iron oxide being superparamagnetic, the ratio of polymer to iron being 0.1 to 0.5 (w/w), said particles having sedimentation constants in the range of 150–5000S, said particles having at least one of the following magnetic properties:

a) specific power absorption rate (SAR) greater than 300 w/g Fe, measured in an electromagnetic field of 1 MHz frequency and 100 Oe field strength;

b) initial magnetic susceptibility greater than 0.7 EMU/gFe/Gauss; and c) magnetic moment greater than $10^{-15}$ erg/Gauss.

2. A composition according to claim 1 wherein the polymer is dextran.

3. A composition according to claim 1 wherein the specific power absorption rate is greater than 350 W/g Fe.

4. A composition according to claim 1 wherein the polymer-iron ratio is 0.2–0.4 (w/w).

5. A composition according to claim 1 wherein the particles have sedimentation constants in the range of 500–2500S.

6. A composition according to claim 1 wherein the particles have at least two of the magnetic properties set forth in claim 1.

7. A composition according to claim 1 wherein the particles have all three of the magnetic properties set forth in claim 1.

8. A composition according to claim 3 wherein the particles have at least one of the properties b) and c) set forth in claim 1.

9. A composition according to claim 1 wherein the particles further comprise a particle-encapsulating lipid.

10. A composition according to claim 9 wherein the particle-encapsulating lipid comprises an antibody or antibody fragment.

11. A composition according to claim 9 wherein the particle-encapsulating lipid has a transition temperature in the range of 41°–54° C.

12. A composition according to claim 11 wherein the particle-encapsulating lipid further comprises a therapeutic agent.

13. A method for heating a tissue comprising contacting said tissue with the composition of claim 1, then exposing said tissue to an oscillating electro-magnetic field at a frequency of 0.5–1.5 MHz and a field strength of 75–150 Oe.

* * * * *

UNITED STATES PATENT AND TRADEMARK OFFICE
CERTIFICATE OF CORRECTION

PATENT NO. : 5,411,730
DATED : May 2, 1995
INVENTOR(S) : Dmitri Kirpotin; Daniel C.F. Chan; Paul A. Bunn It is certified that error appears in the above-indentified patent and that said Letters Patent is hereby corrected as shown below:

At column 1, line 2, please delete "grant No. 2531781" and replace with --Contract No. CA58187--.

Signed and Sealed this

Seventh Day of November, 1995

Attest:

BRUCE LEHMAN

*Attesting Officer*    Commissioner of Patents and Trademarks